(12) United States Patent
Delmotte et al.

(10) Patent No.: US 7,226,657 B1
(45) Date of Patent: Jun. 5, 2007

(54) ELEMENT PROVIDED WITH A FIBRIN LAYER, PREPARATION AND USE THEREOF

(75) Inventors: Yves Delmotte, Neufmaison (BE); Nathalie Belot, Nivelles (BE); Pierre Vermeulen, Lillois (BE); Nicole Tasiaux, Brussels (BE)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/831,121

(22) PCT Filed: Nov. 4, 1999

(86) PCT No.: PCT/US99/25955

§ 371 (c)(1),
(2), (4) Date: Aug. 16, 2001

(87) PCT Pub. No.: WO00/25838

PCT Pub. Date: May 11, 2000

(30) Foreign Application Priority Data

Nov. 4, 1998 (BE) .................................. 9800796

(51) Int. Cl.
*B32B 3/06* (2006.01)
(52) U.S. Cl. ................. 428/306.6; 428/308.4; 428/316.6; 428/315.5; 428/315.7; 428/315.9
(58) Field of Classification Search ............ 428/316.6, 428/306.6, 308.4, 315.5, 315.7, 315.9
See application file for complete search history.

(56) References Cited

U.S. PATENT DOCUMENTS 2,533,004 A 12/1950 Ferry et al.
2,576,006 A 11/1951 Ferry et al.
3,523,807 A 8/1970 Gerendas
3,641,240 A 2/1972 Hymes et al.

(Continued)

FOREIGN PATENT DOCUMENTS

DE   DE 38 41 397 C2   11/1992

(Continued)

OTHER PUBLICATIONS

The Use of Fibrin Paper and Forms in Surgery, S.C. Harvey, Boston Mediacl & Surgical Journal, May 4, 1916, vol. CLXXIV, No. 1S, pp. 658-659.

(Continued)

*Primary Examiner*—Hai Vo
(74) *Attorney, Agent, or Firm*—Bell, Boyd & Lloyd LLC

(57) ABSTRACT

An element provided with a layer based on fibrin- or fibrinogen-containing material, said element comprising (a) a hydrophobic or substantially hydrophobic support, which has a porous part with a thickness of 0.1 to 5 mm, and whose pores, extending across its thickness have a node spacing of 5 to 100 μm, one face of said porous part being treated with a compound based on fibrin and/or a fibrinogen-containing material, and (b) a fibrin-based layer covering said treated surface of the support, characterized in that said fibrin-based layer is substantially uniform and homogeneous on said treated surface, and that the fibrin layer and at least the face of the support in contact with the fibrin layer are substantially free of fibrinogen.

44 Claims, 11 Drawing Sheets

U.S. PATENT DOCUMENTS

| | | |
|---|---|---|
| 3,723,244 A | 3/1973 | Breillatt, Jr. |
| 4,016,877 A | 4/1977 | Cruz, Jr. et al. |
| 4,066,083 A | 1/1978 | Ries |
| 4,116,898 A | 9/1978 | Dudley et al. |
| 4,148,664 A | 4/1979 | Cruz, Jr. |
| 4,225,580 A | 9/1980 | Rothman et al. |
| 4,238,480 A | 12/1980 | Sawyer |
| 4,359,049 A | 11/1982 | Redl et al. |
| 4,442,655 A | 4/1984 | Stroetmann |
| 4,505,817 A | 3/1985 | Blomback et al. |
| 4,505,822 A | 3/1985 | Blomback et al. |
| 4,537,767 A | 8/1985 | Rothman et al. |
| 4,548,736 A | 10/1985 | Müller et al. |
| 4,578,067 A | 3/1986 | Cruz, Jr. |
| 4,587,018 A | 5/1986 | Blomback et al. |
| 4,600,533 A | 7/1986 | Chu |
| 4,606,337 A | 8/1986 | Zimmermann et al. |
| 4,621,631 A | 11/1986 | Paques et al. |
| 4,631,055 A | 12/1986 | Redl et al. |
| 4,640,778 A | 2/1987 | Blomback et al. |
| 4,655,980 A | 4/1987 | Chu |
| 4,675,361 A | 6/1987 | Ward, Jr. |
| 4,683,142 A | 7/1987 | Zimmermann et al. |
| 4,689,399 A | 8/1987 | Chu |
| 4,690,684 A | 9/1987 | McGreevy et al. |
| 4,704,131 A | 11/1987 | Noishiki et al. |
| 4,720,512 A | 1/1988 | Hu et al. |
| 4,725,671 A | 2/1988 | Chu et al. |
| 4,760,131 A | 7/1988 | Sundsmo et al. |
| 4,786,556 A | 11/1988 | Hu et al. |
| 4,833,200 A | 5/1989 | Noishiki et al. |
| 4,837,285 A | 6/1989 | Berg et al. |
| 4,872,867 A | 10/1989 | Joh |
| 4,874,368 A | 10/1989 | Miller et al. |
| 4,882,148 A | 11/1989 | Pinchuk |
| 4,909,251 A | 3/1990 | Seelich |
| 4,911,926 A | 3/1990 | Henry et al. |
| 4,932,942 A | 6/1990 | Maslanka |
| 4,948,540 A | 8/1990 | Nigam |
| 4,978,336 A | 12/1990 | Capozzi et al. |
| 5,019,393 A | 5/1991 | Ito et al. |
| 5,049,393 A | 9/1991 | Noon et al. |
| 5,053,048 A | 10/1991 | Pinchuk |
| 5,071,644 A | 12/1991 | Viegas et al. |
| 5,080,893 A | 1/1992 | Goldberg et al. |
| 5,112,615 A | 5/1992 | Ito et al. |
| 5,126,140 A | 6/1992 | Ito et al. |
| 5,140,016 A | 8/1992 | Goldberg et al. |
| 5,153,003 A | 10/1992 | Kurihara et al. |
| 5,156,613 A | 10/1992 | Sawyer |
| 5,167,960 A | 12/1992 | Ito et al. |
| 5,182,317 A | 1/1993 | Winters et al. |
| 5,201,745 A | 4/1993 | Tayot et al. |
| 5,209,776 A | 5/1993 | Bass et al. |
| 5,213,580 A | 5/1993 | Slepian et al. |
| 5,223,420 A | 6/1993 | Rabaud et al. |
| 5,242,792 A * | 9/1993 | Rudolph et al. ............... 435/2 |
| 5,244,799 A | 9/1993 | Anderson |
| 5,260,420 A | 11/1993 | Burnouf-Radosevich et al. |
| 5,272,074 A * | 12/1993 | Rubens ....................... 435/180 |
| 5,278,200 A | 1/1994 | Coury et al. |
| 5,292,362 A | 3/1994 | Bass et al. |
| 5,324,647 A | 6/1994 | Rubens et al. |
| 5,364,622 A | 11/1994 | Franz et al. |
| 5,368,563 A | 11/1994 | Lonneman et al. |
| 5,376,376 A | 12/1994 | Li |
| 5,376,692 A | 12/1994 | Park et al. |
| 5,395,923 A | 3/1995 | Bui-Khac et al. |
| 5,412,076 A | 5/1995 | Gagnieu |
| 5,418,222 A | 5/1995 | Song et al. |
| 5,447,724 A | 9/1995 | Helmus et al. |
| 5,455,040 A | 10/1995 | Marchant |
| 5,486,357 A | 1/1996 | Narayanan |
| 5,521,280 A | 5/1996 | Reilly et al. |
| 5,525,348 A | 6/1996 | Whitbourne et al. |
| 5,541,167 A | 7/1996 | Hsu et al. |
| 5,541,305 A | 7/1996 | Yokota et al. |
| 5,567,806 A | 10/1996 | Abdul-Malak et al. |
| 5,578,073 A | 11/1996 | Haimovich et al. |
| 5,580,923 A | 12/1996 | Yeung et al. |
| 5,744,515 A * | 4/1998 | Clapper ....................... 523/113 |
| 5,824,080 A * | 10/1998 | Lamuraglia .................. 424/423 |
| 5,882,354 A * | 3/1999 | Brauker et al. ............. 424/423 |
| 5,989,215 A | 11/1999 | Delmotte et al. |
| 6,056,970 A | 5/2000 | Greenawalt et al. |
| 6,074,663 A | 6/2000 | Delmotte et al. |
| 6,162,241 A | 12/2000 | Coury et al. |
| 6,210,667 B1 | 4/2001 | Reed |
| 6,262,236 B1 | 7/2001 | Edwardson et al. |
| 6,262,255 B1 | 7/2001 | Mares-Guia |

FOREIGN PATENT DOCUMENTS

| | | |
|---|---|---|
| EP | 0 068 149 A2 | 1/1983 |
| EP | 0 085 166 A1 | 8/1983 |
| EP | 0 103 290 A2 | 3/1984 |
| EP | 0 166 263 A1 | 1/1986 |
| EP | 0 187 894 A1 | 7/1986 |
| EP | 0 213 563 B1 | 3/1987 |
| EP | 0 262 890 A2 | 4/1988 |
| EP | 0 369 764 A2 | 5/1990 |
| EP | 0 372 969 A1 | 6/1990 |
| EP | 0 479 615 A1 | 4/1992 |
| EP | 0 485 210 A2 | 5/1992 |
| EP | 0 485 210 A3 | 5/1992 |
| EP | 0 534 178 A2 | 3/1993 |
| EP | 0 562 864 A1 | 9/1993 |
| EP | 0 611 571 A1 | 2/1994 |
| EP | 0 592 242 A1 | 4/1994 |
| FR | 2 448 900 | 1/1980 |
| WO | WO 89/02445 A1 | 3/1989 |
| WO | WO 91/01711 A1 | 2/1991 |
| WO | WO 91/19519 A1 | 12/1991 |
| WO | WO 92/15341 A1 | 9/1992 |
| WO | WO 92/22312 A1 | 12/1992 |
| WO | WO 93/19805 A1 | 10/1993 |
| WO | WO 93/21971 A1 | 11/1993 |
| WO | WO 94/02182 A1 | 2/1994 |
| WO | WO 94/22503 A1 | 10/1994 |
| WO | WO 96/17638 A1 | 6/1996 |
| WO | WO 96/22115 A1 | 7/1996 |
| WO | WO 96/39212 A2 | 12/1996 |
| WO | WO 00/25838 A1 | 5/2000 |

OTHER PUBLICATIONS

Fibrin Clots, Fibrin Films, and Fibrinogen Plastics, John D. Ferry and Peter R. Morrison, Harvard Medical School, Feb. 17, 1994, Paper No. 22, pp. 566-572.

Fibrin Films in Neurosurgery, With Special Reference to Their Use in the Repair of Dural Defects and in the Prevention of Meningocerebral Adhesions, Orville T. Bailey and Franc D. Ingraham, Harvard Medical School, Feb. 17, 1944, Paper No. 27, pp. 597-600.

Use of Thrombin and Fibrinogen in Skin Grafting, Lieutenant Eugene P. Cronkite et, al., J.A.M.A., Apr. 1, 1944, vol. 124, No. 14, pp. 976-978.

Preparation and Properties of Serum and Plasma Proteins, IX Human Fibrin in the Form of an Elastic Film, John D. Ferry and Peter R. Morrison, Harvard Medical School, Feb. 1947, Paper No. 48, vol. 69, pp. 400-409.

Fibrin Gel Limits Intra Abdominal Adhesion Formation, Gary W. Chmielewski, et al., The American Surgeon, Sep. 1992, vol. 58, No. 9, pp. 590-593.

Fibrin as a Haemostatic In Cerebral Surgery, Ernest G. Grey, Surgery, Gynecology and Obstetrics, pp. 452-454.

Plasma Clot Suture of Nerves, I.M. Tarlov, M.D., et al., Archives of Surgery, pp. 44-58.

The Prevention and Treatment of Intestinal Adhesions, John E. Connolly, M.D., et al., International Abstracts of Surgery, May 1960, vol. 110, No. 5, pp. 417-431.

The Binding of Human Fibrinogen to Native and Fraction Fibrins and the Inhibition of Polymerization of a New Human Fibrin., A.L. Copley and B. W. Luchini, Life Sciences, 1964, vol. 3, No. 11, pp. 1293-1305.

Stable Complex of Fibrionogen and Fibrin, Takeru Sasaki, et al., Science, May 20, 1966, vol. 152, pp. 1069-1071.

An Evaluation of the Bionite Hydrophili Contact Lens for Use in a Drug Delivery System, Yvonnet Maddox, B.S. and Howard N. Bernstein, M.D., Annals of Ophthalmology, Sep. 1972, pp. 789-790, 793-794, 796, 798, 802.

Treatment of Stress Incontinence by a Fibrin Bioplas, Bela Horn, et al., British Journal of Obstetrics and Gynecology, Jan. 1975, vol. 82, pp. 61-63.

Effect of a Biologic Glue on the Leakage Rate of Experimental Rectal Anastomoses, Hisashi Oka, MD., et al., The American Journal of Surgery, May 1982, vol. 143, pp. 561-564.

In Vitro Properties of Mixtures of Fibrin Seal and Antibiotics, H. Ridi, G. Schlag. et al., Biomaterials, Jan. 1984, vol. 4, pp. 29-32.

Fibrin Gels and Their Possible Implication for Surface Hemorheology in Health and Disease, Birger Blomback and Masahisa Okada, Annals New York Academy of Sciences, 1983, pp. 397-409.

The Tisseel Method, History Background Application Techniques and Indication of "Fibrin Sealing", in Modern Surgery, Lukas Giovanettoni, Immuno, Jan. 1985, pp. 1-70.

Studies on Prevention of Intra-Abdominal Adhesion Formation by Fibrin Sealant, Svend Lindenberg, et al. Acta Chir Scand, 1985, 151, pp. 525-527.

Localized Prevention of Postsurgical Adhesion Formation and Reformation with Oxidized Regenerated Cellulose, Takao Shimanuki, et al., Journal of Biomedical Materials Research, 1987, vol. 21, pp. 173-185.

The Use of Sprayed Fibrin Glue for Face Lifts, D. Marchac E. Pugash and D. Gault, European Journal of Plastic Surgery, 1987, vol. 10, pp. 139-143.

Reduced Human Peritoneal Plasminogen Activating Activity: Possible Mechanism of Adhesion Formation, J.N. Thompson, et al., British Journal Surgery, Apr. 1989, vol. 76, No. 4, pp. 382-384.

Fibrin Glue Inhibits Intra-abdominal Adhesion Formation, Christian de Virgilio, et al., Archives of Surgery, Oct. 1990, vol. 125, pp. 1378-1382.

Die Anwendung des Fibrinklebers zur Prophylaxe und Therapie intraabdomineller Adhasionen, W. Brands, Th. Diehm, et al., Der Chirurg, 1990, vol. 61, pp. 22-26.

The Need for Intensive Study of Pericardial Substitution After Open Heart Surgery, Shlomo Gabbay, Trans Am Soc Artificial Internal Organs, 1990, vol. XXXVI, pp. 789-791.

Dura Covered wtih Fibrin Glue Reduces Adhesions in Abdominal Wall Defects, F. Schier, et al., European Journal of Pediatric Surgery, 1991, pp. 343-345.

The Effect of Fibrin Glue and Peritoneal Grafts in the Prevention of Intrapertioneal Adhesions, J.F.H. Gauwerky, et al., Archives of Gynecology and Obstetrics, 1990, vol. 247, pp. 161-166.

Effects of Fibrin Sealant on Tubal Anastomosis and Adhesion Formation, Togas Tulandi, M.D., Fertility and Sterility, Jul. 1991, vol. 56, No. 1, pp. 136-138.

Alteration in Pericardial Adhesion Formation Following Pretreatment with Fibrin Glue, Douglas H. Joyce, et al., Journal of Applied Biomaterials, 1991, vol. 2, pp. 269-271.

Prophylaxis of Pelvic Sidewall Adhesions With Gore-Tex Surgical Membrane, a Multicenter Clinical Investigation, The Surgical Membrane Study Group, Fertility & Sterililty, Apr. 1992, vol. 57, No. 4, pp. 921-923.

Effectiveness of Two Barriers at Inhibiting Post-radical Pelvic Surgery Adhesions, F.J. Montz, et al., Gynecologic Oncology, 1993, vol. 48, pp. 247-251.

Inhibition of Intra-abdominal Adhesions: Fibrin Glue in a Long Term Model, Barry B. Sheppard, M.D. et al., The American Surgeon, Dec. 1993, vol. 59, No. 12, pp. 786-790.

Properties and Prevention of Adhesions Applications of Bioelastic Materials, D.W. Urry, et al., Mat. Res. Soc. Symp. Proc., 1993, vol. 292.

Expanded-polytetrafluoroethylene But Not Oxidized Regenerated Cellulose Prevents Adhesion Formation and Reformation in a Mouse Uterine Horn Model of Surgical Injury, A.F. Haney, M.D., Fertility & Sterility, Sep. 1993, vol. 60, No. 3, pp. 550-558.

Fibrin Sealant Adhesive Systems: A Review of Their Chemistry, Material Properties and Clinical Applications, David H. Sierra, Journal of Biomaterials Applications, Apr. 1993, vol. 7, pp. 309-352.

Prevention of Postoperative Adhesions in the Rat by In Situ Photopolymerization of Bioresorbable Hydrogel Barriers, Jennifer L. Hill-West, et al., Obstetrics & Gynecology, Jan. 1994, vol. 83, No. 1, pp. 59-64.

Fibrin Sealant in Laparoscopic Adhesion Prevention in the Rabbit Uterine Horn Model, PierAndrea De Iaco, M.D., et al., Fertility and Sterility, Aug. 1994, vol. 62, No. 2, pp. 400-494.

Prevention of Surgical Adhesions Using Aerosoled Biodegradable Polyesters, SM Fujita, et al: The 20th Annual Meeting of the Society for Biomaterials, Apr. 5-9, 1994.

Tissue Adhesives in Wound Healing, Dale S. Feldman and David H. Sierra, University of Alabama at Birmingham, May 1994, pp. 1-38.

Adhesion Reduction in the Rabbit Uterine Horn Model Using an Absorbable Barrier, TCD-7, Cary B. Linsky, Ph.D., et al., The Journal of Reproductive Medicine, Jan, 1987, vol. 32, No. 1, pp. 17-20.

* cited by examiner

ELEMENT PROVIDED WITH A FIBRIN LAYER, PREPARATION AND USE THEREOF

The invention relates to an element having a fibrin-based layer, said element comprising (a) a hydrophobic or substantially hydrophobic support which has a porous part with a thickness of 0.1 to 5 mm, and whose pores, extending across its thickness, have a node spacing of 5 to 100 µm, one face of said porous part being treated with a fibrin and/or fibrinogen-based compound, and (b) a fibrin-based layer covering said treated face of the support.

Such elements are known from WO96/07444 and from U.S. Pat. No. 5,298,255. These known elements are prepared by simply immersing a support in a solution containing fibrinogen and thrombin or by pushing such solution through a porous support. These known elements, when prepared by simple immersion, have a substantially compact fibrin layer and have little or no fibrin in the support pores, or have fibrin in the pores having greater diameters and substantially no fibrin in the pores having smaller diameters, due to an easier passage of fibrin through the pores with greater diameters. This easier passage of fibrin through the pores with greater diameters causes a lack of homogeneity and/or uniformity.

Such lack of homogeneity or uniformity with respect to the presence of fibrin in the support pores has proved, in some cases, to affect cell attachment.

This invention aims at obviating these drawbacks and essentially relates to an element as described in the first paragraph of this specification, said element being characterized in that said fibrin-based layer is substantially uniform and homogeneous on said treated surface. The fibrin layer according to the present invention is characterized by the lack of fibrinogen, unbound from the fibrin layer. The lack of fibrinogen on the fibrin layer may be detected by the absence of the γ band in the electrophoresis diagram. The lack of fibrinogen in the fibrin layer is caused by the fact that any fibrinogen which has not reacted to form is the fibrin layer is sucked through the porous support. Hence, the element according to the invention is characterized in that, at the contact surface between the fibrin layer and the support, there is substantially preferably no fibrinogen which has not reacted. For example, the fibrin layer of the element according to the invention contains less than 2% by weight of fibrinogen which has not reacted to form a fibrin network, preferably less than 1%, particularly less than 0.5% and more particularly less than 0,1%.

Advantageously, the fibrin layer and at least a support layer extending across a thickness of 10 µm contains less than 1% by weight, advantageously less than 0.5%, preferably less than 0.1% by weight of fibrinogen which has not reacted, with respect to the weight of the fibrin layer. Preferably, fibrin extends across the thickness of the treated porous part of the support, from said treated face to a depth of at least 2 µm, both through the pores having an average diameter of 10 to 20 µm and through the pores having an average diameter of more than 20 µm.

In accordance with a particular embodiment, in which the porous part of the support has a substantially homogeneous and uniform porosity over the treated face, some fibrin extends homogeneously and uniformly across the thickness of the porous part of the support to a depth of at least 10 µm. According to a possible embodiment, the porous support contains fibrinogen in a layer which is at a distance of more than 10 µm from the face in contact with the fibrin layer, particularly to a depth of 20 µm.

The presence of free fibrinogen (having not reacted yet) has to be preferably avoided when the fibrin network has been already formed, in order to prevent new fibrin bonds from forming in the network upon reimmersion of the dried fibrin layer, such bonds reducing the size of the alveoli or of some alveoli of the network.

According to one embodiment of the invention, some of the fibrin attached to the network extends across the thickness of the treated porous part of the support, from said treated surface to a depth of at least 2 µm, through the pores having an average diameter of 10 to 20 µm and through the pores having an average diameter above 20 µm. Although the support may be made of any hydrophobic or substantially hydrophobic material, it is particularly made of polyethylene, of polyethylene therephthalate or of polytetrafluoroethylene, said materials being advantageously stretched, particularly in both axial directions.

The term hydrophobic or substantially hydrophobic material is used herein to identify materials having a bias of 30 to 50°, which bias is measured with the method ASTM D 2578-84.

Advantageously, the porous part of the support has a substantially homogeneous and uniform porosity over the treated surface, i.e. the pore distribution or number by surface unit is substantially uniform for the porous part. For example, given one porous part, the volume of the pores having a diameter of more than 10 µm in an area of 1 cm$^2$ of the porous part varies from 0.8 to 1,2, preferably from 0.9 to 1.1 times the average volume of pores having a diameter of more than 10 µm, for each cm2 of the porous part.

According to one embodiment, at least the face of the fibrin layer opposite to the one contacting the porous support is stabilized. Particularly, said fibrin-based layer is at least partially cross-linked, to form a network of adjacent alveoli, having apertures therebetween. The layer is advantageously sufficiently cross-linked not to be water-soluble. According to a detail of one advantageous embodiment, said layer is provided with cells and/or proteins, particularly with is proteins mediating cell-fibrin bonds, with fibronectin, etc.

Although the thickness of the fibrin layer, when it is hydrated and re-hydrated may be of more than 100 µm, or even of more than 150 µm, according to a characteristic of one preferred embodiment, the cross-linked fibrin-based layer (in the hydrated or post-hydration state) which covers the porous part of the support is 0.5 to 100 µm thick, advantageously 2.5 to 50 µm thick, preferably 5 to 20 µm thick, with alveoli being formed between the cross-linked fibrin-based molecules or bonds, said alveoli having a volume of 5 to 25 µm$^3$, the average thickness or height of said chamber being of 1 to 5 µm, particularly of 1 to 3 µm.

According to a detail of one particular embodiment, the pores of the support part, covered by said fibrin layer have inner faces at least partially covered by a water-soluble or substantially water-soluble protein. For example the pores of the support part covered by said fibrin layer are partially covered by fibrinogen, albumin, fibronectin, vibronectin, or by a mixture thereof. Particularly, the support face opposite to the treated face is at least partially covered by a water-soluble or substantially water-soluble protein. Such covering is advantageous to improve the adhesion of tissues in contact with the face opposite to the treated face of the support.

In accordance with an advantageous characteristic, at least the pores of the porous part of the support are at least partially covered by a water-soluble or miscible polar additive. Such additive is preferably non-denaturing for protein and biocompatible structures. Such additives may include glycerol, sugars (sucrose, mannitol, sorbitol, etc.). Said additives are particularly soluble or at least miscible in water and are particularly selected amongst water-soluble or miscible additives allowing to lower the freezing temperature as compared with the water freezing temperature at atmospheric pressure.

According to a preferred embodiment, the element is dry, for example having a moisture content of less than 0.5% by weight, or even of less than 0.1% by weight.

According to an advantageous embodiment, the fibrin layer is cross-linked in presence of fibronectin. The cross-linked fibronectin content in the fibrin layer is advantageously of 0.5 to 15%, preferably of 1 to 10%, of the fibrin and fibronectin weight in the cross-linked layer. This content corresponds to the weight of fibronectin bonds in the layer as compared to the weight of fibrin and fibronectin bonds of the layer.

According to a detail of an advantageous embodiment, the fibrin layer contains calcium, particularly calcium and chlorine, more precisely calcium chloride. The calcium content of the fibrin layer, expressed in µg of calcium by volume unit of the fibrin layer (cm3) is advantageously of 1 to 100 µg/cm$^3$, preferably of 5 to 90 µg/cm$^3$, particularly of 10 to 50 µg/cm$^3$. The chlorine content in the fibrin layer is advantageously of 1.5 to 200 µg/cm$^3$, preferably of 8 to 170 µg/cm$^3$, particularly of 16 to 100 µg/cm$^3$. When calcium is in the form of calcium chloride, the calcium chloride content in the fibrin layer (expressed in µg of calcium chloride by volume unit (cm$^3$) of the fibrin layer) is advantageously of 2.5 to 300 µg/cm$^3$, preferably of 13 to 260 µg/cm$^3$, particularly of 26 to 150 µg/cm$^3$.

Advantageously, the fibrin layer substantially contains no further salts of alkali or alkaline-earth metals in addition to calcium chloride.

Preferably, the content of salts of alkali or alkaline-earth metals differing from the calcium chloride is at least 10 times, preferably 20 times, particularly 50 times smaller than the content of calcium chloride in the fibrin layer.

Although the support may be a porous support whatsoever, the element support is preferably a biocompatible and/or biodegradable support.

According to a particular detail of one embodiment of the element in accordance with the invention, the element has two or more superposed fibrin layers. Advantageously, the layers have alveoli with different average volumes. Particularly, the fibrin layer which covers the fibrin layer in contact with the porous support has alveoli with a smaller average volume as compared with the average volume of the alveoli of the fibrin layer in contact with the porous support. For example, the average volume of alveoli in the fibrin layer which covers the fibrin layer in contact with the support is of less than about 0.5 times the average volume of alveoli in the fibrin layer in contact with the support. According to one embodiment, the fibrin layer covering the fibrin layer in contact with the support partially penetrates said fibrin layer in contact with the support. The penetration of the fibrin layer with small alveoli in the fibrin layer with large alveoli is advantageously such that the fibrin layer with small alveoli penetrates at least 50% of the thickness of the fibrin layer with large alveoli, but preferably less than the whole thickness.

The fibrin of the layer of the element of the invention, as well the fibrin present in the porous substrate is substantially not denatured, preferably not denatured.

The invention also relates to a process for preparing an element according to the invention.

This process provides that:
at least one porous part of a first face of a porous support is brought into contact with an aqueous solution containing fibrin or fibrinogen, or with one or more fibrin-based of fibrinogen-containing compounds,
the face of the porous part of the support opposite to said first face is homogeneously and uniformly submitted to a suction force to suck the solution, at least partly, through said porous part, thus ensuring the deposition of a layer based on fibrin or on fibrinogen-containing materials, homogeneously and uniformly with respect to said porous part, and the diffusion of at least the solution water through the porous part of the porous support as well as the penetration of fibrin or fibrinogen-containing materials through the porous support. Such suction provides a fibrin layer which is substantially free of fibrinogen, particularly if the fibrin layer has been washed with water or with an aqueous solution. Advantageously, the suction of the solution through the porous material is carried out at least during the cross-linking of fibrin, and preferably at least during the reaction of the fibrinogen-containing material and the cross-linking of the fibrin. The fibrin present in the porous material is therefore advantageously cross-linked with the fibrin layer covering the said first face of the porous material.

The process according to the invention provides an element which complies therewith, as described hereinbefore.

Thanks to suction, the fibrin attached to the network is arranged to penetrate the porous support to a depth of at least 2 µm, both in the pores having an average diameter of 10 to 20 µm and in the pores having an average diameter of more than 20 µm.

Advantageously, the face of the support opposite to said first face, is submitted to a pressure of less than $0.8\ 10^5$ Pa, and a pressure difference is created between the two faces of the porous part of at least $0.3\ 10^5$ Pa. Preferably, the support face opposite to said first face is submitted to a pressure of less than $0.5\ 10^5$, preferably less than or equal to $0.4\ 10^5$ Pa. According to a preferred embodiment, while providing an efficient passage of fibrin or fibrinogen across the thickness of the porous part of the support, the support face opposite to the first face is intermittently submitted to a first pressure, of less than $0.8\ 10^5$ Pa, preferably less than $0.4\ 10^5$ Pa, said first pressure being at least 5% higher than the second pressure. Instead of varying the positive or negative pressure on the face opposite to said first face, it would be possible to slightly vary the pressure exerted on said first face.

Advantageously, the face of the porous support opposite to said first face is submitted to a pressure of less than $0.8\ 10^5$ Pa, and exposed to a temperature of 0 to 100° C., preferably to a temperature of 15 to 60° C., particularly to a temperature of 25 to 40° C.

According to a variant of the process according to the invention, the face of the porous support opposite to said first face is submitted to a solution selected so as to create a reverse osmosis, causing the diffusion of at least the solution water in contact with the first face through the porous part of the support. Such diffusion ensuring thereby a substantially uniform and regular passage of fibrin or fibrinogen at least partially through the thickness of the porous support.

For implementing the process of the invention, a solution containing fibrinogen-containing materials and thrombin is advantageously first prepared and after preparation contacted with the porous material. Thereafter, the solution is at least partly sucked through the porous material. Preferably, substantially immediately after mixing the fibrinogen containing material and thrombin, the solution is contacted with the porous material and preferably sucked through the porous material. For example, a solution containing fibrinogen containing material and thrombin is prepared in continue by mixing a solution of fibrinogen containing material with a thrombin containing solution, and after its preparation (substantially immediately after its preparation), the said solution is contacted with the porous material. This is advantageous for ensuring a good distribution of the thrombin in the solution in contact with the porous material.

For implementing the process according to the invention, a solution is advantageously used which contains 5 to 20 mg/ml of fibrinogen-containing materials, particularly a solution which contains 5 to 20 mg/ml of fibrinogen-containing materials and 0.01 to 10 units of thrombin per ml, preferably a solution which contains 5 to 20 mg/ml of fibrinogen-containing materials, factor XIII, and 0.01 to 2, preferably 0.05 to 1 units of thrombin per ml. According to an advantageous embodiment, the solution contains less than 0.5 units of thrombin per ml.

Advantages have also been noted with a solution containing 0.1 to 10 units of factor XIII per ml. Advantageous results have also been obtained from a solution containing 1 to 40 millimoles of $CaCl_2$/ml, particularly 1 to 20 millimoles of $CaCl_2$/ml to reduce or slow down fibrinolysis. Hence, for example, for a fibrin layer prepared with 20 millimoles of $CaCl_2$/ml, no fibrinolysis was visually detected one week after the fibrin layer had been prepared.

It will be noted that smaller quantities of thrombin used in the formation of the fibrin network correspond to larger amounts of fibrinogen which can penetrate the porous support. In spite of this, the process according to the invention provides a fibrin layer substantially free of fibrinogen, particularly at the face of the support which is in contact with the fibrin layer.

According to a characteristic of a process according to the invention, during a first step, at least one portion of a first face of a porous support is placed into contact with a solution containing fibrin and/or fibrinogen-containing materials, while the face of the porous support opposite to said first face is homogeneously and uniformly submitted to a suction force, thus ensuring a diffusion of at least the solution water across the thickness of the porous support and a penetration of fibrin or fibrinogen-containing materials in the porous support to a depth of at least 2 μm, homogeneously and uniformly with respect to said porous part of the first face and, during a second step, the fibrin and/or fibrinogen layer is stabilized.

In accordance with a possible embodiment, a contact is provided between said part of the first face and a moving aqueous solution.

Advantageously, the solution containing fibrin or materials containing fibrinogen also contains a polar organic additive. The use of such polar organic additive has proved to allow the control of fiber thickness in the fibrin network. Moreover, the presence of such organic additive has also provided advantages in the protection of the fibrin-based layer during the drying step, which may be possibly provided after a washing step. The drying operation is advantageously effected at least partially by lyophilization, advantageously at a temperature of −30° C. and −100° C., preferably at a temperature of −40° C. to −70° C. For example, the drying operation is performed in several steps, i.e. a first drying step for raising temperature (for example at a temperature of 30 to 70° C.) or for creating a vacuum after removal of the fibrin or fibrinogen-containing material solution in contact with the porous part of the support, and a second drying step for lyophilization.

Drying operations are advantageously performed after one or more washing steps, by means of water, an aqueous solution, e.g. an aqueous solution containing a polar organic additive (e.g. in the order of 1 to 20% by weight, particularly in the order of 5 to 10% by weight), such as glycerin. A particular washing operation consists in bringing the fibrin layer integral with the porous support in contact with an aqueous solution, particularly a solution containing glycerol (e.g. 1 to 20% by weight, particularly 5 to 10% by weight) and thereafter in submitting the other face of the support to a suction force, to suck the solution through the porous support. Such washing operation provides a fibrinogen-free porous support. This operation may be performed on supports provided with a fibrin layer which are not compliant with the invention, thereby allowing to turn a product obtained by a simple contact of the porous support with the fibrinogen-containing solution into an element according to the invention.

The solution of fibrin or of fibrinogen-containing materials used in the process for forming the fibrin layer according to the invention preferably contains 0 to 20%, particularly 3 to 15%, and more particularly 5 to 10% of said polar organic additive. This additive may advantageously be glycerol, a sugar (mannitol, sorbitol, sucrose, glucose, etc.). When using a solution which contains fibrinogen-containing materials in the order of 5 to 20 mg/ml, thrombin in the order of 0.01 to 10 units/ml and 5 to 10% of glycerol in the process according to the invention, a network of fibrin fibers was obtained, wherein the size of the alveoli is similar to that in the network obtained with a solution which contains fibrinogen-containing materials in the order of 5 to 20 mg/ml, thrombin in the order of 0.01 to 10 units/ml (without glycerol) in the process according to the invention. Nevertheless, the fiber size in the network obtained by using glycerol was smaller, whereby a better use of fibrin or fibrinogen-containing materials in the solution resulted when using glycerol.

The pH of the solution of fibrin or of fibrinogen-containing materials is advantageously of 5 to 8.5, preferably of 5.5 to 8, particularly of 6 to 7.5. The pH of the solution may be controlled by means of a buffer solution (e.g. a tris buffer), by adding a strong (HCl) or weak acid, of mineral or organic origin (citric acid, etc.).

The solution also advantageously contains at least a water-soluble protein, particularly albumin.

According to one particular embodiment, at least for a part of the deposit of the fibrin- or fibrinogen compounds-based layer, the concentration of fibrin or fibrinogen compounds in the solution in contact with the first face is controlled in order to ensure a substantially constant water diffusion through the support.

In the process according to the invention, a biocompatible or biodegradable porous support is used.

According to a particular embodiment, wherefrom advantages are obtained to ensure from the start a substantially uniform water diffusion through the thickness of the porous support, the porous part is treated with an aqueous solution which advantageously contains a wetting agent and/or a water-soluble protein and/or a polar organic additive, before bringing the fibrin- or fibrinogen-containing solution in contact with said porous part.

According to the invention, the porous support may be also treated, successively, with a solution which contains fibrin or fibrinogen-containing materials to deposit several fibrin layers. According to the invention, the porous support may be treated with a solution which contains fibrin or fibrinogen-containing materials but does not contain thrombin, and then the pretreated support may be treated with a solution containing thrombi n.

The invention also relates to a filter including a filtering membrane consisting of an element according to the invention, to a bioreactor including a membrane consisting of an element according to the invention, an implant consisting of an element according to the invention, and an artificial skin produced from an element according to the invention.

Since glycerol has been found to be useful for controlling the size of alveoli, for a better use of fibrin (thinner fibers) and for ensuring a better viability of the cells attached to the fibrin network, another object of the invention is a compound based on fibrin or on fibrinogen-containing materials, said compound having the form of a dry foam or of particles of dry foam, containing 0.05 to 10% by weight of a water-soluble or miscible polar organic additive, said foam having a porosity consisting of at least 50% by volume of chambers or volume cavities of 5 to 25 µm2. Advantageously, at least 90% by weight of fibrin is in cross-linked form. Possibly, the compound also contains one or more proteins and/or one or more active substances. Amongst polar additives, glycerin is preferred, but other additives may be also used, such as sugars, sucrose, glucose, mannitol, etc. The water content is advantageously lower than 0.5% by weight. In fact the foam or cross-linked fibrin network is at least partially covered by a water-soluble or miscible polar organic additive.

The preparation of this compound may be effected in a process wherein, possibly after a pre-drying step, an aqueous solution of fibrin and/or fibrinogen, also containing a water-soluble or miscible polar organic additive, is dried by lyophilization, the organic solvent content of said solution being of 0.05 to 10% by weight, so as to obtain a compound containing less than 0.5% thereof by weight. Advantageously, the drying operation by lyophilization is effected at a temperature of −40 to −100° C., preferably of −50° C. to −75° C. Particularly, lyophilization is performed in three steps, each step involving a temperature decrease of the compound or solution to a temperature of −40 to −100° C., followed by a pressure decrease to less than 0.4 bar (0.4 $10^5$ Pa). For example, in a first step, pressure is lowered to a pressure of 0.2 to 0.4 $10^5$ Pa, and in the last step, pressure is decreased to less than 0.2 $10^5$ Pa.

The invention also relates to a process allowing to extract the unbound fibrinogen from the fibrin layer, and particularly the fibrinogen which is found in the porous support, in such a way as to obtain a fibrinogen-free fibrin layer, and particularly a porous support and a fibrin layer both free of fibrinogen. This process provides that:

at least one part of the fibrin layer attached on a first face of the porous support is brought to contact with an aqueous solution advantageously containing a polar organic additive, and the face of the porous support opposite to said first face is homogeneously and uniformly submitted to a suction force to suck the solution, at least partly, through said porous part, thus ensuring the removal of fibrinogen in the proximity of said first face of the support, homogeneously and uniformly with respect to said porous part. Thanks to this suction, at least the solution water is diffused through the thickness of the porous part of the porous support. If this process is applied for a sufficient time, the amount of water diffused through the thickness of the porous part can be sufficient to remove or extract the fibrinogen in the pores of the porous support. Therefore, this suction provides a substantially fibrinogen-free fibrin layer, or even a porous support and a fibrin layer free of fibrinogen.

This washing process, when using an aqueous solution which contains one or more additives, e.g. one or more soluble proteins, one or more drugs, etc, allows the introduction in the porous support of a certain amount of said additive/s, or the covering of the face of the support which is not in contact with the fibrin layer with said additive/s.

Thanks to the solution suction, water is allowed to penetrate the porous support, so that, for example, at a depth of at least 2 µm from the first face (face bearing the fibrin layer), advantageously of at least 10 µm, preferably of at least 20 µm, at least the pores having an average diameter of 10 to 20 µm are free of fibrinogen.

Advantageously, the face of the porous support opposite to said first face is submitted to a pressure of less than 0.8 $10^5$ Pa, and a pressure difference of at least 0.3 $10^5$ Pa is created between the two faces of the porous part. Preferably, the face of the porous support opposite to said first face is submitted to a pressure of less than 0.5 $10^5$ Pa, more preferably less than or equal to 0.4 $10^5$ Pa. According to a preferred embodiment, while providing an efficient passage of water across the thickness of the porous part of the support, the face of the porous support opposite to the first face is intermittently submitted to a first pressure of less than 0.8 $10^5$ Pa, preferably less than about 0.4 $10^5$ Pa, and to a second pressure of less than 0.8 $10^5$ Pa, preferably less than 0.4 $10^5$ Pa, the first pressure being at least 5% higher than the second pressure. Instead of varying the positive or negative pressure on the face opposite to said first face, it would be possible to slightly vary the pressure exerted on said first face.

Advantageously, the face of the porous support opposite to said first face is submitted to a pressure of less than 0.8 $10^5$ Pa, and to a temperature of 0 to 100° C., preferably to a temperature of 15 to 60° C., particularly to a temperature of 25 to 40° C.

According to a variant of the process according to the invention, the face of the porous support opposite to said first face is submitted to a solution selected so as to create a reverse osmosis, causing the diffusion of at least the solution water in contact with the first face through the porous part of the support. Such diffusion ensuring thereby a substantially uniform and regular passage of water at least partially through the thickness of the porous support.

A further object of the invention is a process for preparing porous supports covered by a layer made of a bioabsorbable material or of an absorbable polymer, particularly of a polylactic polymer and/or of polyglycol polymers and/or of biopolymers, as well as structural proteins and polysaccharides, said structural proteins being selected in the group including collagen, elastin, fibronectin, laminin and fibrin, and other proteins forming human or animal tissues, as well as recombinant proteins. This process provides that an aqueous solution or suspension is prepared, which contains one or more polymers and/or biopolymers and/or materials to form said polymers and/or biopolymers on site. This solution or suspension is brought to contact with a first face of a porous support, while sucking at least a part of the water of said solution or suspension from at least one different face of the porous support (advantageously the face opposite to the first face). This suction force causes water and advantageously absorbable biopolymers or polymers to be diffused in the porous support. In order to ensure such diffusion, the face of the porous support opposite to said first face (face in contact with the solution or suspension) is submitted to a pressure of less than 0.8 $10^5$ Pa, while a pressure difference is created between the two faces of the porous part of at least $0.3 \cdot 10^5$ Pa. Preferably, the support face opposite to said first face is submitted to a pressure of less than $0.5 \cdot 10^5$ Pa, preferably less than or equal to $0.4 \cdot 10^5$ Pa. According to a preferred embodiment, providing an efficient passage of water through the thickness of the porous part of the support, the face of the support opposite to the first face is intermittently submitted to a first pressure, of less than $0.8 \cdot 10^5$ Pa, preferably less than $0.4 \cdot 10^5$ Pa, and to a second pressure, of less than $0.8 \cdot 10^5$ Pa, preferably less than $0.4 \cdot 10^5$ Pa, the first pressure being at least 5% higher than the second pressure. Instead of varying the positive or negative pressure on the face opposite to said first face, it would be possible to slightly vary the pressure exerted on said first face. Said face opposite to the face in contact with the polymer solution or suspension might also be submitted to the influence of a solution selected so as to create a reverse osmosis, causing the diffusion of at least the solution water in contact with the first face through the porous part of the support. Such diffusion ensuring thereby a substantially uniform and regular passage of water at least partially through the thickness of the porous support. The solution diffusing through the porous support advantageously is at a temperature of 20 to 70° C., particularly of 30 to 50° C. Once the layer of absorbable polymers or biopolymers is formed, this layer is advantageously dried by lyophilization. Lyophilization is advantageously effected as described with respect the fibrin layer. If drying operations are performed by lyophilization, the solution used to form the layer advantageously contains a polar additive, particularly glycerol, for example in the order of 1 to 15%, particularly of 5 to 10%.

Further characteristics and details will be apparent from the following detailed description of certain embodiments, wherein reference is made to the annexed drawings. In these drawings, FIG. 1 is a diagrammatic view of an element according to the invention;

FIGS. 3, 4 and 5 are cross-sectional views of a slice of fibrin networks, as taken with an electron microscope (Philips XL20 Scanning Electron Microscope), with a magnification of 5,000 times, before lyophilization, whereas

Figure 9:
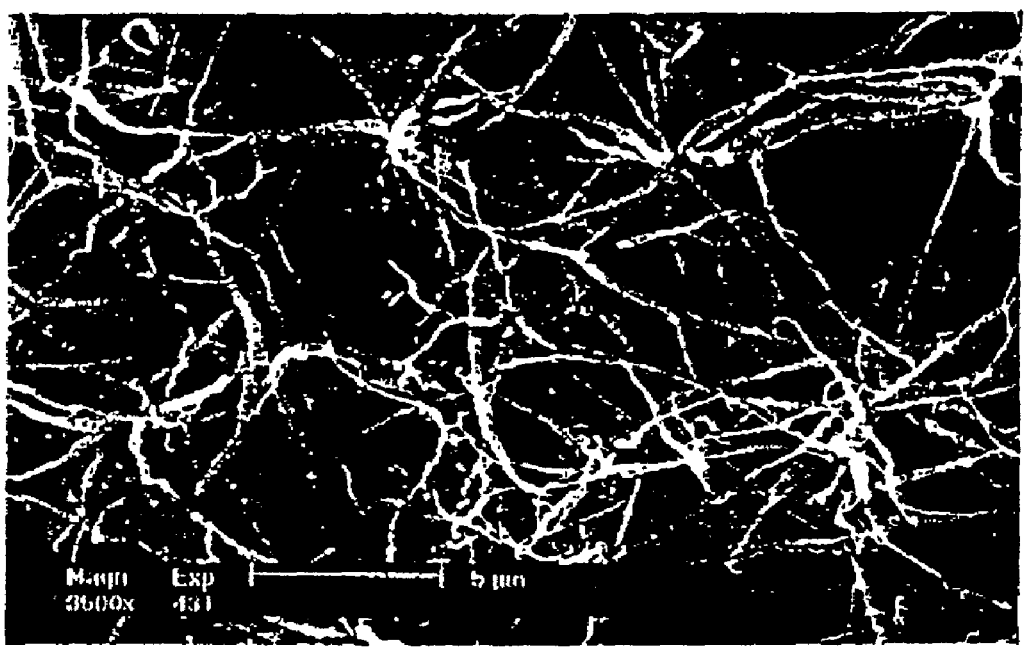
Figure 10:
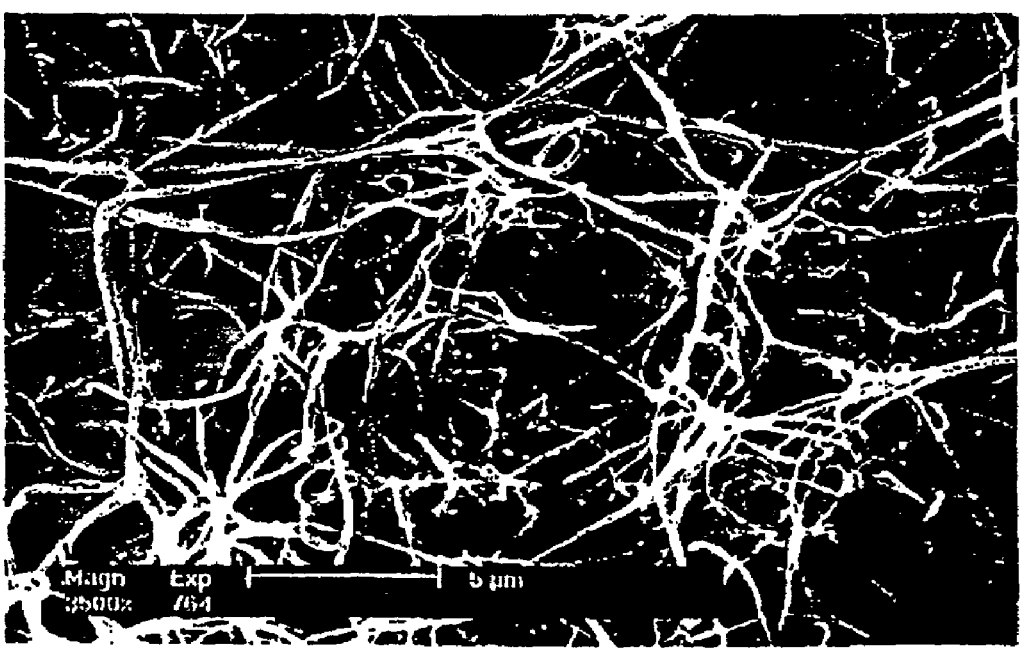
Figure 11:
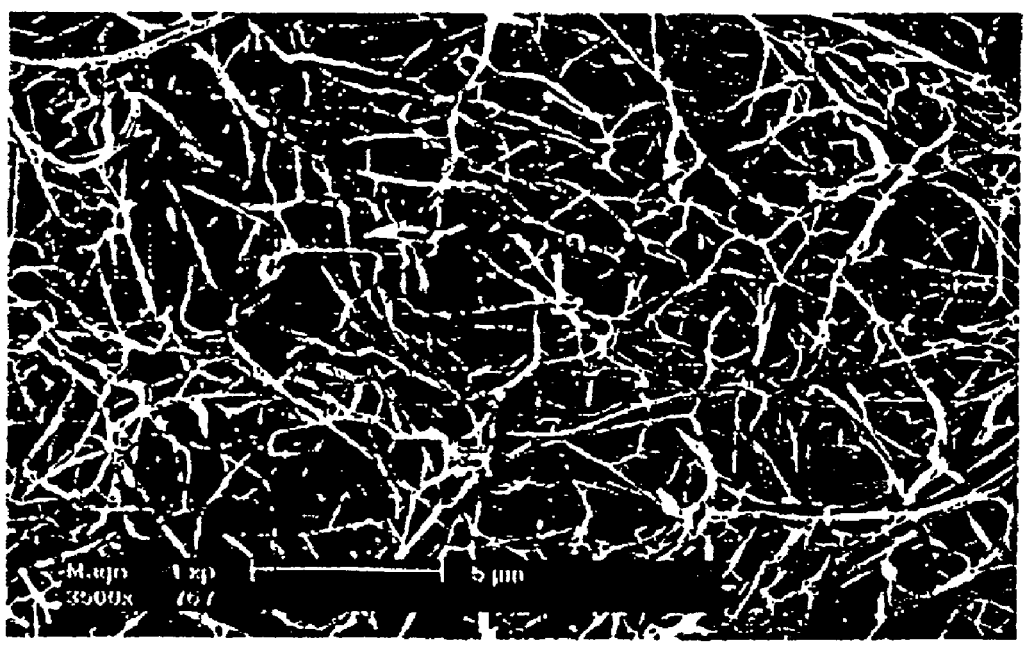
Figure 12:
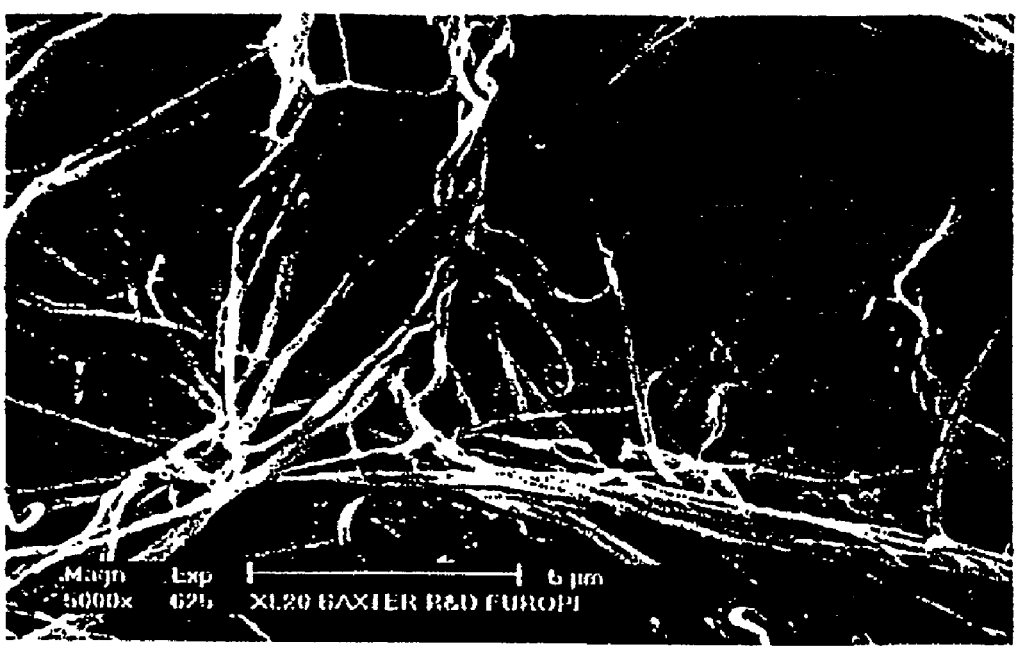
Figure 13:
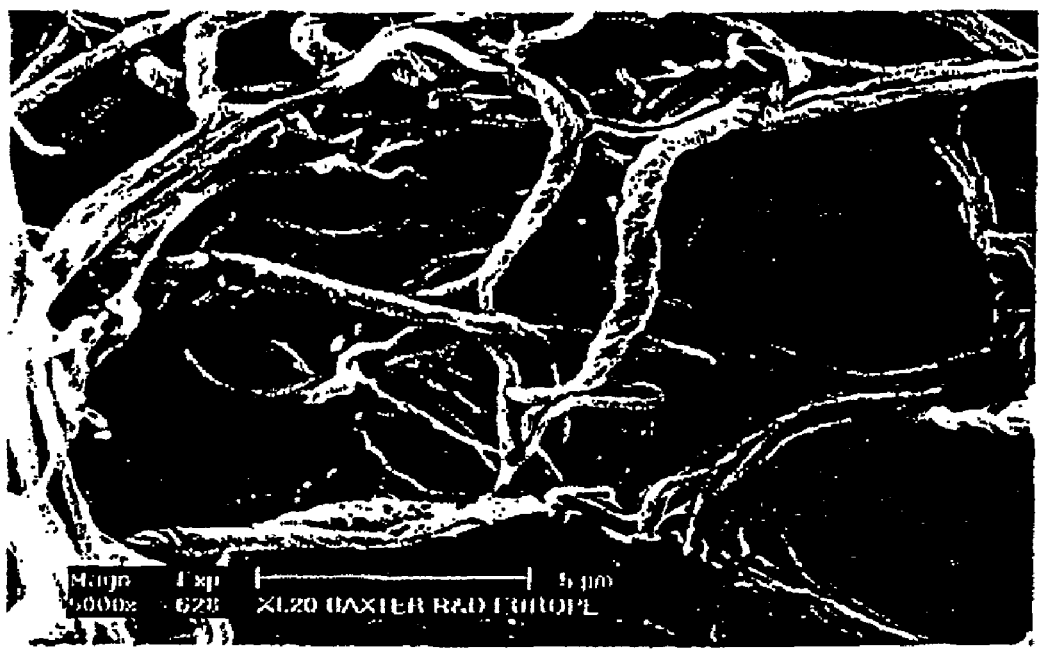
Figure 14:
Figure 15:
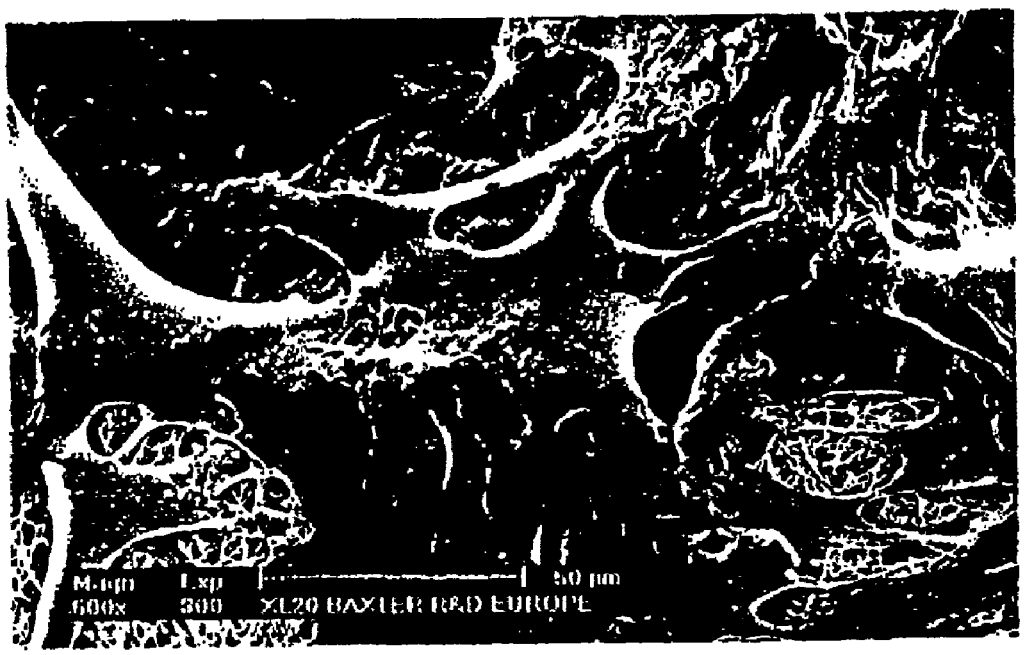
Figure 16:
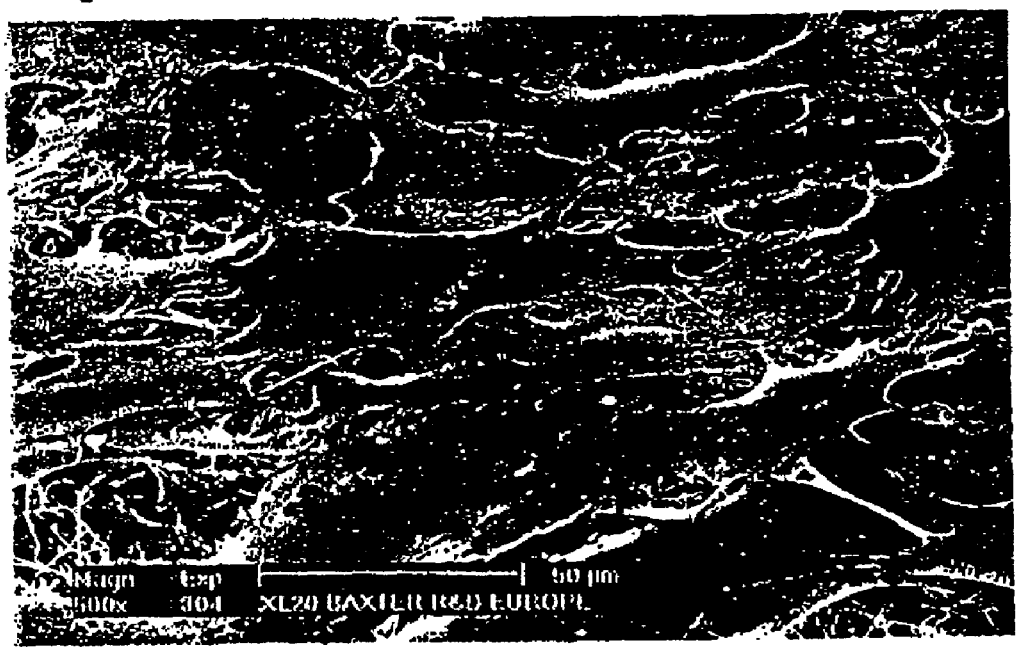
Figure 17:
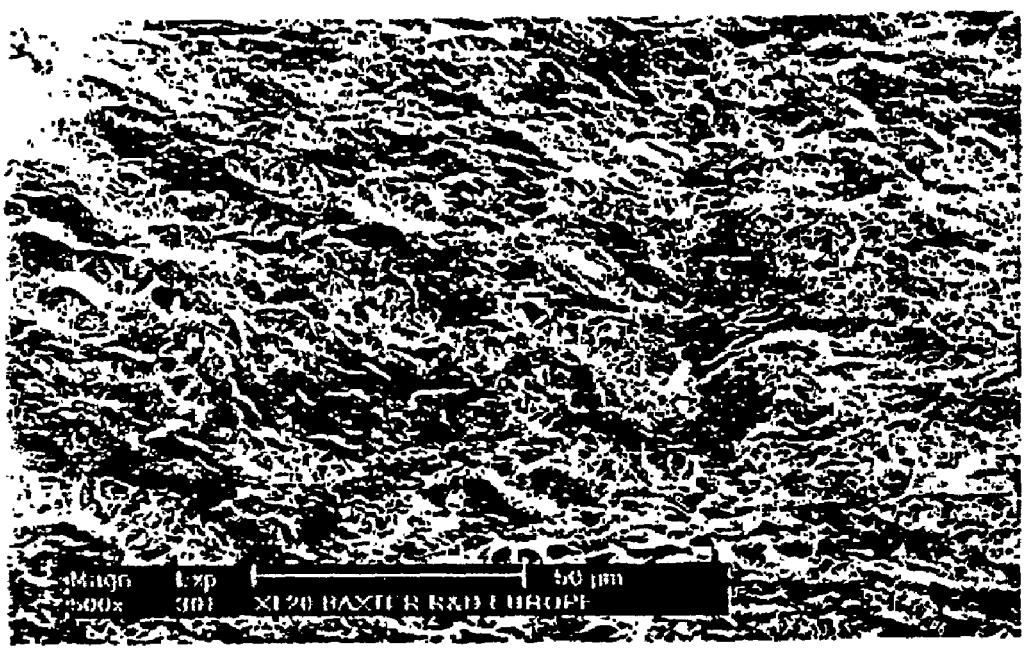
Figure 18:
Figure 19:
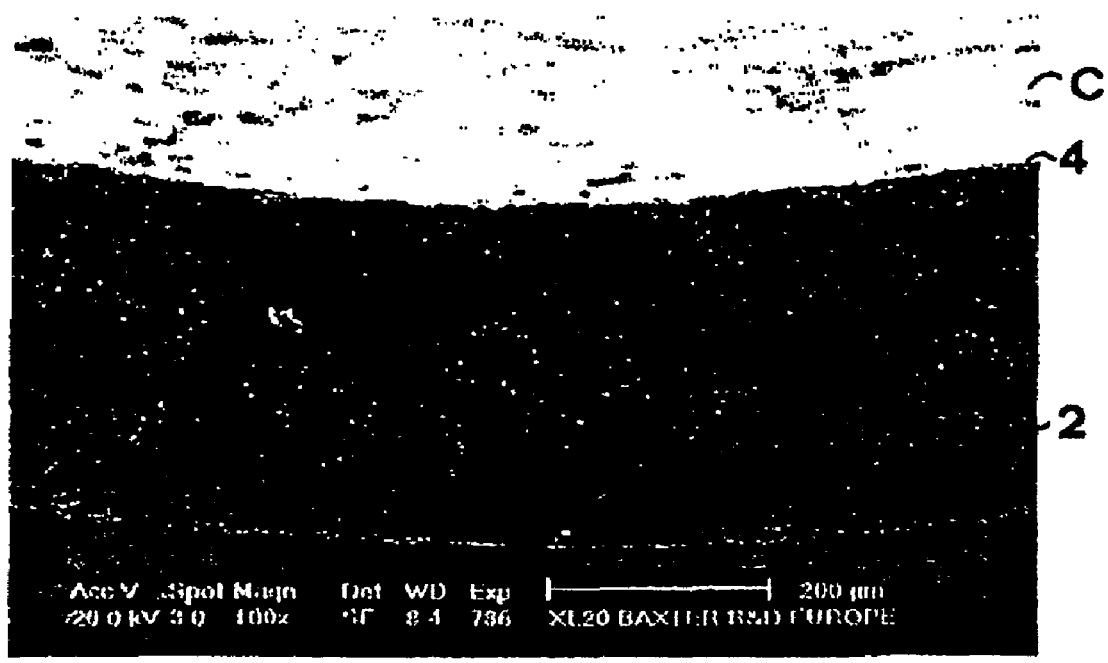
Figure 20:
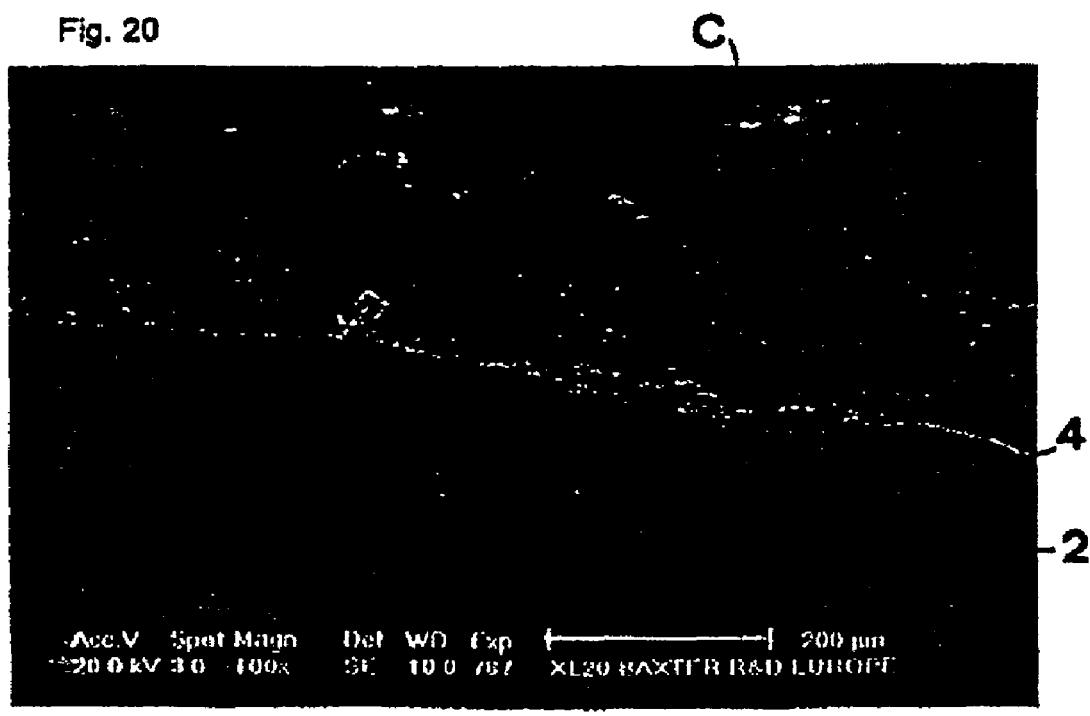
Figure 21:
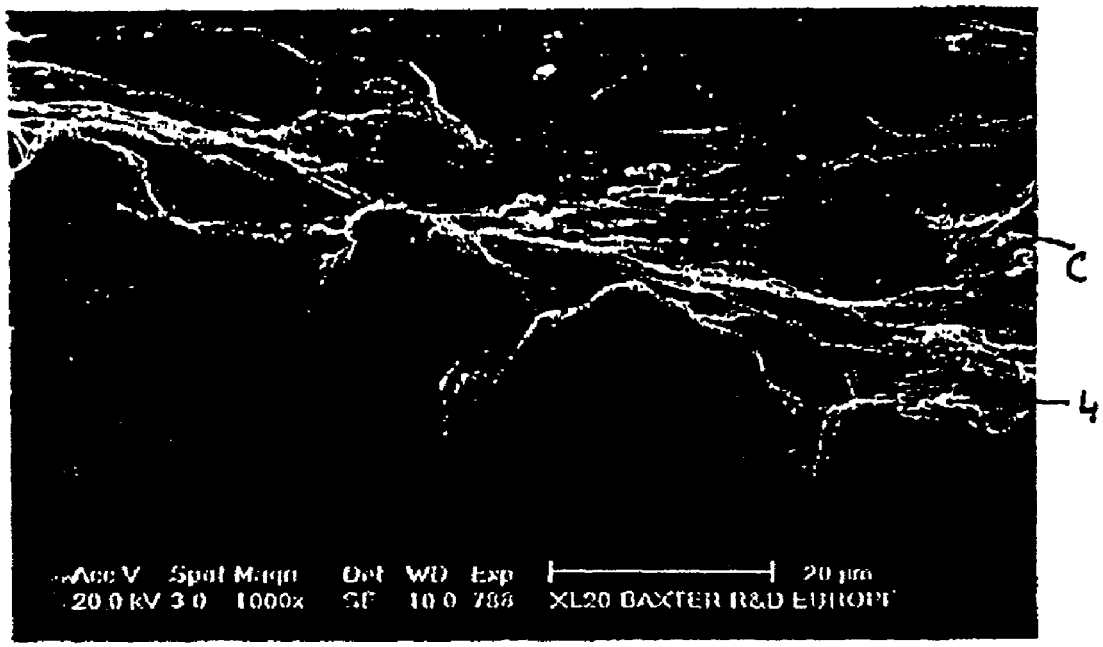
Figure 22:
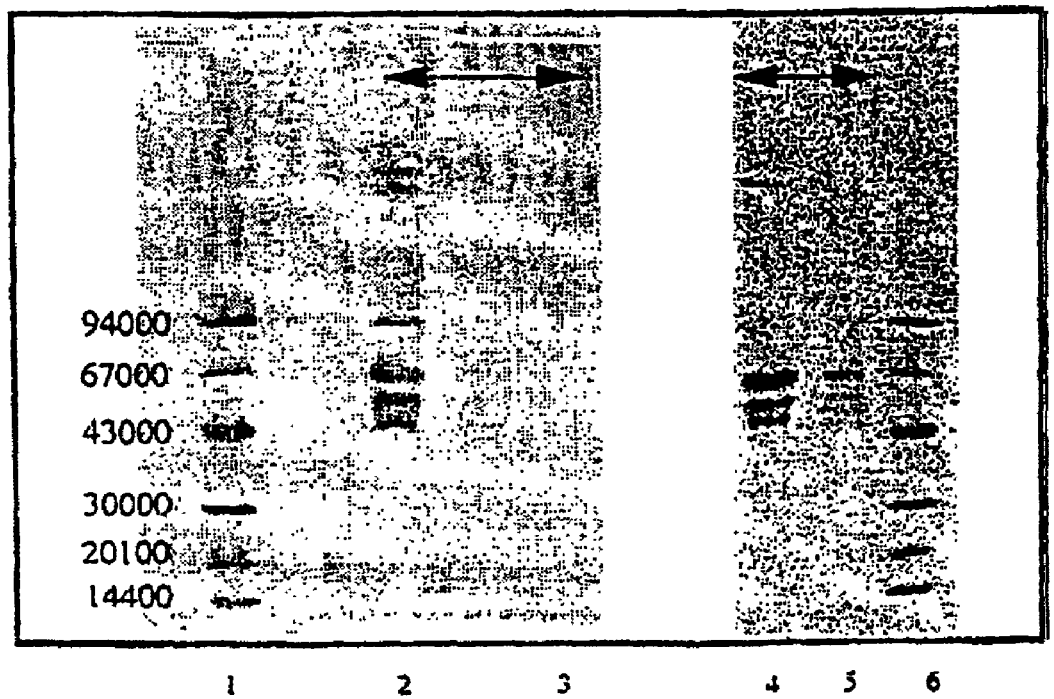

FIGS. 9, 10 and 11 are cross-sectional views of the networks obtained by means of a solution containing 1 IU/ml, 10 IU/ml and 20 IU/ml of thrombin respectively, as seen in cross section;

FIGS. 12 to 14 are cross-sectional views of networks obtained by means of a solution containing no $CaCl_2$ (FIG. 12), 2.7 mM $CaCl_2$/ml (FIG. 13) and 27 mM $CaCl_2$/ml (FIG. 14), as taken with an electron microscope (Philips XL20), with a magnification of 5,000 times;

FIGS. 15, 16, 17 and 18 are top views of the fibrin networks with cells after two hours of culture, as taken with an electron microscope (Philips XL20 Scanning Electron Microscope), with a magnification of 500 times;

FIGS. 19 to 21 are cross sectional views of a porous support 2, bearing a fibrin layer 4, with cells "C", as taken with an electron microscope, with a magnification of 100 times, 100 times and 1000 times respectively;

FIG. 22 is an electrophoresis diagram of markers having a low molecular weight (1, 6), of control fibrinogen (5), of control fibrin (4), of the polymer layer from the exudate (the part passing through the porous membrane) after incubation, and of the floating part of the exudate after incubation.

Figure 1:
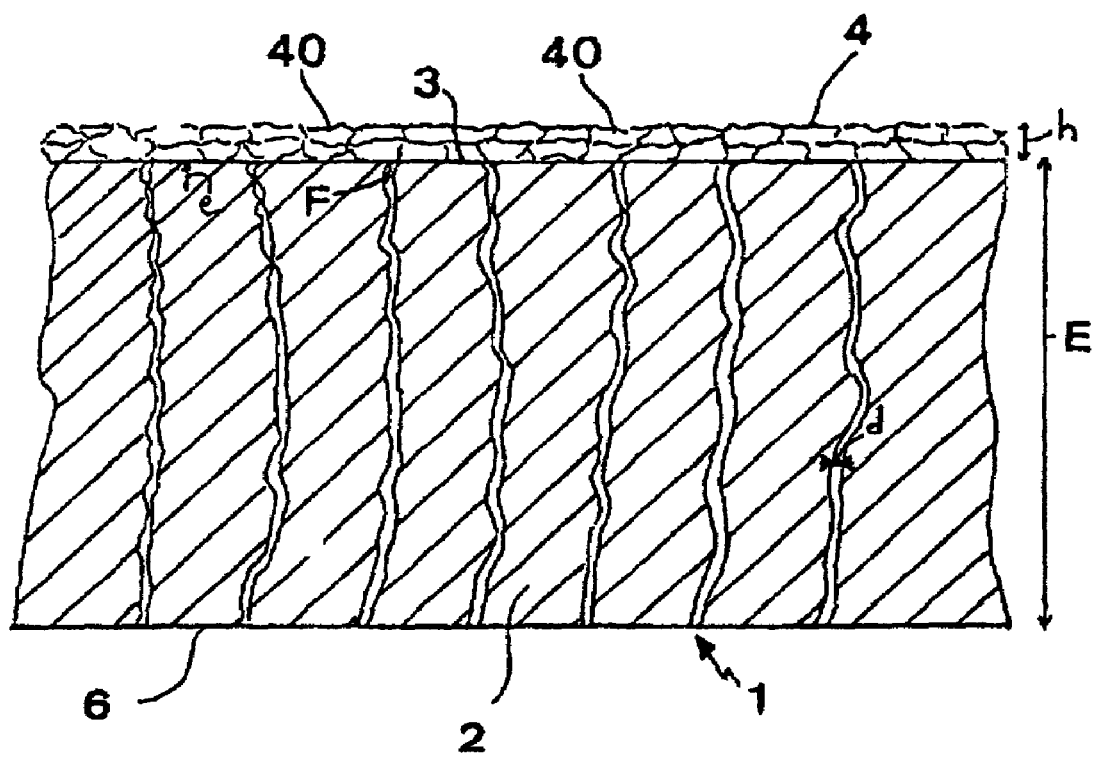

FIG. 1 diagrammatically shows a sectional, larger-scale view of one part of an element according to the invention.

The element 1 comprises (a) a hydrophobic or substantially hydrophobic support 2, for example PTFE (expanded and stretched in both axial directions), which has a porous part with a thickness E of 0.1 to 5 mm, e.g. of 300 to 500 µm, and whose pores P, extending across its thickness have an average diameter "d" (porous volume/surface of pores) of 5 to 100 µm, e.g. of about 30 to 40 µm, one face 3 of said porous part of said support 2 being treated with a fibrin-and/or fibrinogen-based compound, and (b) a fibrin-based layer 4 covering said treated surface 3 of the support 2.

Said fibrin-based layer 4 is substantially uniform and homogeneous on said treated face 3. After being washed, the fibrin layer 4 contains no fibrinogen. For example, the content of fibrinogen in the layer 4 (fibrinogen unbound from the fibrin layer) is below 0.5% by weight; preferably below 0.1% by weight of the fibrin layer.

Some fibrinogen F may extend across the thickness E of the treated porous part of the support, from said treated face to a depth "e" of at least 10 µm both in the pores having an average diameter of 10 to 20 µm (pores whose volume, expressed in µm³, divided by the surface of the pore walls, expressed in µm³, gives 10 to 20 µm) and in the pores having an average diameter of more than 20 µm. Particularly, in all the pores of more than 25 µm of the treated face of the porous part, some fibrinogen extends across the thickness E of the support to a depth "e" of at least 30 µm. Nevertheless, at the is face 3, the support is substantially free of fibrinogen unbound from the network. The lack of fibrinogen unbound from the fibrin network is due to the passage of water through the porous support. In one particular embodiment, the porous support is free of fibrinogen to a depth of at least 10 µm, from the face bearing the fibrin layer. According to a particularly advantageous embodiment, the support is free of fibrinogen throughout its thickness.

The fibrin layer 4, as shown in FIG. 1, is stabilized by cross-linkage due to the presence of factor XIII. Hence, said layer 4 forms a network of adjacent alveoli 40.

The thickness "h" of the fibrin layer as determined from the face 3 (in its dehydrated form) is, for example, of about 10 µm, while the average volume of a chamber or cell is of the order of 10 µm³. The alveoli are open and have apertures therebetween. The term alveoli defines fibrin-free areas having a volume of more than 5 µm³, surrounded by fibrin bonds. The distribution of alveoli over the layer 4 is substantially regular, that is the volume of the alveoli over an area of 1 cm² of the face 3 covered by the layer 4 is of 0.8 to 1.2 times (preferably of 0.9 to 1.1 times) the average volume of chambers by unit of surface (cm²) of that area. The average height of the chambers, as measured perpendicularly to the face 3 is, for example, of 2 to 3 µm.

The element as shown in FIG. 1 is advantageously in a dry state. The moisture content is, for example, of less than 0.01% by weight, which ensures an excellent preservation and stability of the element. When the element is rehydrated, the fibrin layer inflates, for example, by a factor of more than 1.5, particularly by a factor of 1.6 to 2.5 (the thickness of the fibrin layer after rehydration corresponds to 1.6 to 2.5 times the thickness of the dry fibrin layer).

According to a particular embodiment, the pores P have inner faces at least partially covered by a water-soluble or substantially water-soluble protein and/or the face 6 of the support, opposite to the treated face is at least partially covered by a water-soluble or substantially water-soluble protein. Such covering is advantageous to assist, for example, cell fixation, the adhesion of the tissues surrounding the face opposite to the face treated with fibrin or with fibrinogen-containing materials.

According to an advantageous characteristic of one embodiment, the pores P (inner walls) of the porous part of the support are at least partially covered by a water-soluble or miscible polar organic additive or by traces of such additive. This polar organic additive is advantageously also present at least in part on the fibrin layers of the layer 4 and on the faces 3 and 6 of the support. This additive may be, for example, glycerol, a sugar, etc. or a mixture of these additives. Said additives are particularly soluble or at least miscible in water and are particularly selected amongst water soluble additives allowing the freezing temperature to be lowered with respect to water freezing temperature at atmospheric pressure. The amount of soluble or miscible additive in the fibrin, fibrinogen and/or thrombin solution or in the wet cross-linked fibrin layer (not dried, the water content in the pores is in the order of 50%) is preferably sufficient to lower the freezing temperature at atmospheric pressure of less than $-5°$ C., preferably of less than $-10°$ C.

Although the support of the illustrated embodiment is a biocompatible porous support of PTFE, another biocompatible support can be used, particularly a biodegradable support, or a biocompatible and biodegradable support.

A few examples of processes for preparing an element according to the invention will be described hereafter.

Figure 2:
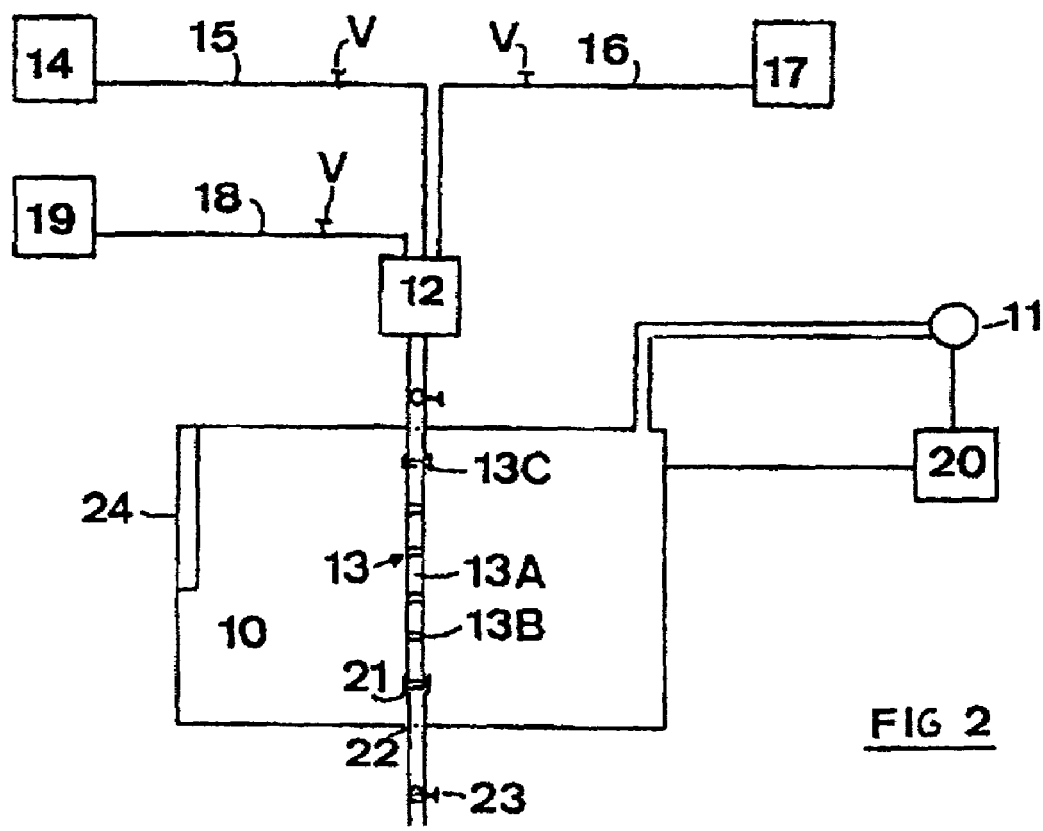
FIG. 2 is a diagrammatic view of an installation for preparing an element according to the invention.

For the preparation of one or more elements according to the invention, a vacuum chamber 10, connected to a vacuum pump 11 has been used to create a vacuum or a negative pressure in the chamber with respect to atmospheric pressure. This chamber is shown diagrammatically in FIG. 2.

The chamber has an intake for letting the solution/s into the inner space or hollow of a tube having an inside diameter of 1 to 100 mm, more particularly of 2 to 10 mm. The tube 13 has porous cylindrical parts 13A (average diameter of pores of 20 to 30 µm) separated by a non-porous ring 13B. The tube thickness was of about 200 to 300 µm for the porous parts. The intake 12 includes the means of fastening an end 13C of the tube thereto in a fluid-tight manner. The intake 12 is connected by means of a duct 15 to a tank 14 which contains an aqueous solution of a fibrinogen-containing material (with a concentration of 10 to 40 mg/ml), including 0.2 to 20 units of factor XIII per ml (IU/ml) and 100 to 1000 µg/ml of fibronectin, by means of a duct 16 to a tank 17 which contains an aqueous solution of thrombin (with a concentration of 0.05 to 2 IU/ml) and by means of a duct 18 to a tank 19 which contains water and possibly one or more additives. The ducts 15, 16 and 18 are fitted with valves V to allow or prevent the passage of a fluid. Said ducts lead one or more fluids towards the intake, depending on atmospheric pressure. A control system 20 controls the vacuum pump operation depending on the desired vacuum and on the vacuum measured inside the chamber.

The tube end opposite to the one fastened to the intake is closed by a plug 21, advantageously extended by a duct 22 with a valve 23, to allow the evacuation of fluids or solutions contained in the tube.

The chamber is also provided with a means 24 to adjust the chamber temperature in the range of $+60°$ C. to $-100°$ C.

EXAMPLE 1

In this example, a solution A, containing 20 mg/ml of a fibrinogen-containing material, 1000 µg of fibronectin per ml and 2 IU/ml of factor XIII, and a solution B, containing 0.2IU of thrombin per ml, and 40 mM (millimoles) of calcium chloride per ml, were used.

The solution A and the solution B were fed into the intake at the same flow rate to obtain a 1:1 mixture of both solutions A and B. The mixture obtained thereby contained 10 mg/ml of fibrinogen, 500 µg/ml of fibronectin, 1 IU/ml of factor XIII, 0.1 IU/ml of thrombin and 20 mM/ml of $CaCl_2$.

The hollow or inner space of the tube was filled with the mixture of solutions A and B, and the chamber pressure was lowered to $0.4 \cdot 10^5$ Pa (that is a negative pressure of about 600 millibar with respect to atmospheric pressure). This vacuum creation causes water to be sucked in through the thickness of the porous parts of the tube. Since the vacuum is created on the outer surface of the tube, the latter is slightly stretched or tightened, which assists the diffusion of liquid through the pores of the tube.

While creating and maintaining vacuum, the outer wall of the tube was found to be wet.

After maintaining the vacuum for about 1 to 30 minutes, the chamber pressure was progressively reset to atmospheric pressure. Once the tube was emptied and washed with water, the inner face of the tube was found to be covered by a cross-linked fibrin layer about 5 µm thick, with chambers or open cells of 15-20 µm³ on the porous parts of the tube (cell height of 2 to 3 µm, area of 5 to 7 µm², as measured parallel to the face of the support bearing the layer). No fibrinogen unbound from the fibrin layer was found in the fibrin layer, nor on the support interface with the fibrin layer. Fibrinogen was found in the pores of the support to a depth (from the inner surface of the tube) of at least about 20 µm for all pores having an average diameter of more than 10 µm.

The passage of fibrinogen through the porous support is confirmed by the electrophoresis diagram of FIG. 22. In fact, some liquid from the face opposite to the one in contact with the fibrinogen solution was collected. After incubating this liquid, electrophoresis peaks were determined both for the polymer layer formed (2) and for the supernatant (3). The result was that, after incubation, the electrophoresis (2) showed fibrin-typical peaks, which proves that fibrinogen had passed through the porous support.

This tube was subsequently dried by a gas heated to $50°$ C.

EXAMPLE 2

Example 1 was repeated, except that the washing step was effected by letting demineralized water flow inside the tube to evacuate the fibrinogen solution, while maintaining a pressure of about $0.4 \cdot 10^5$ Pa in the chamber to ensure a diffusion of washing water through the porous support. This diffusion allows fibrinogen to be removed from the porous support.

EXAMPLE 3

Example 1 was repeated, except that the tube was dried by lowering the tube temperature to $-60°$ C. to turn water into ice and by lyophilizing it at this temperature.

EXAMPLE 4

Example 3 was repeated, except that glycerol was added in the order of 5% by weight of the mixture consisting of 50% of the solution A and 50% of the solution B. It was noted that the presence of glycerol both in the porous support and in the fibrin layer provided a certain flexibility of the element. Further, the lyophilization step was easier.

The presence of glycerol upon formation of the cross-linked fibrin proved to be advantageous for providing a regular and homogeneous structure of the fibrin layer. Moreover, the presence of glycerol assisted the passage of fibrin and fibrinogen in the pores of the porous part of the tube.

EXAMPLE 5

Example 4 was repeated, except that glycerol was added in the order of 10% by weight of the mixture consisting of 50% of solution A and 50% of solution B. It was noted that the presence of glycerol both in the porous support and in the fibrin layer provided a certain flexibility of the element. Further, the lyophilization step was easier.

Some parts of the fibrin networks from examples 2 and 4, before and after lyophilization were left for one night in dishes containing a solution of 2 to 2.5% of glutaraldehyde in dishes. Thereafter, a slice of the network fixed by glutaraldehyde was cut transversely by means of a heated scalpel, which slice was dehydrated by 40%, 50%, 70%, 80%, 90% and 100% ethanol solutions.

Figure 3:
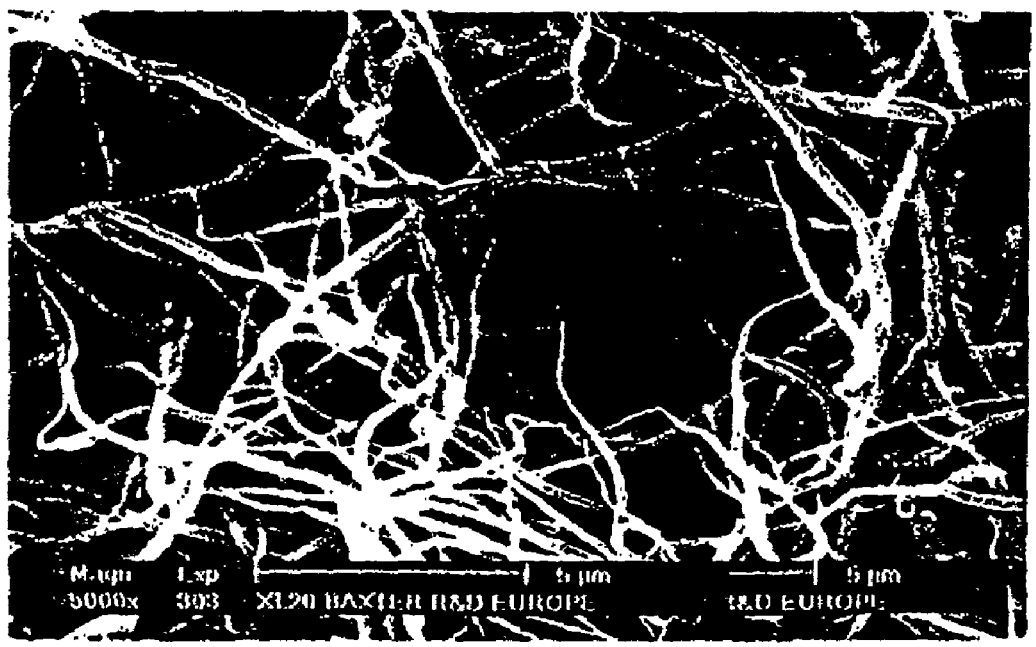
Figure 4:
Figure 5:
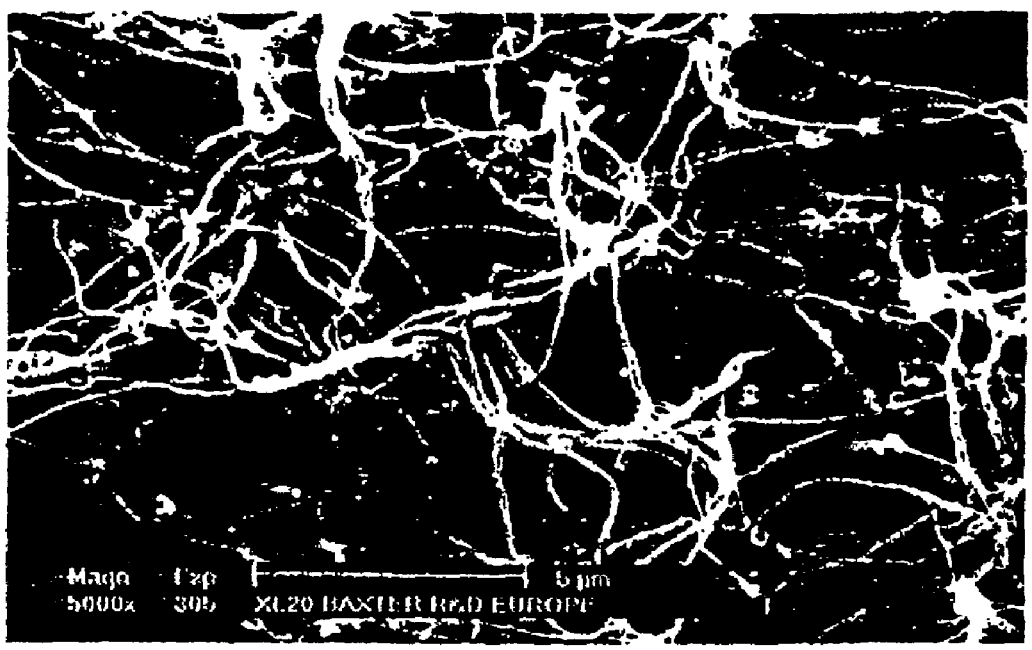
Figure 6:
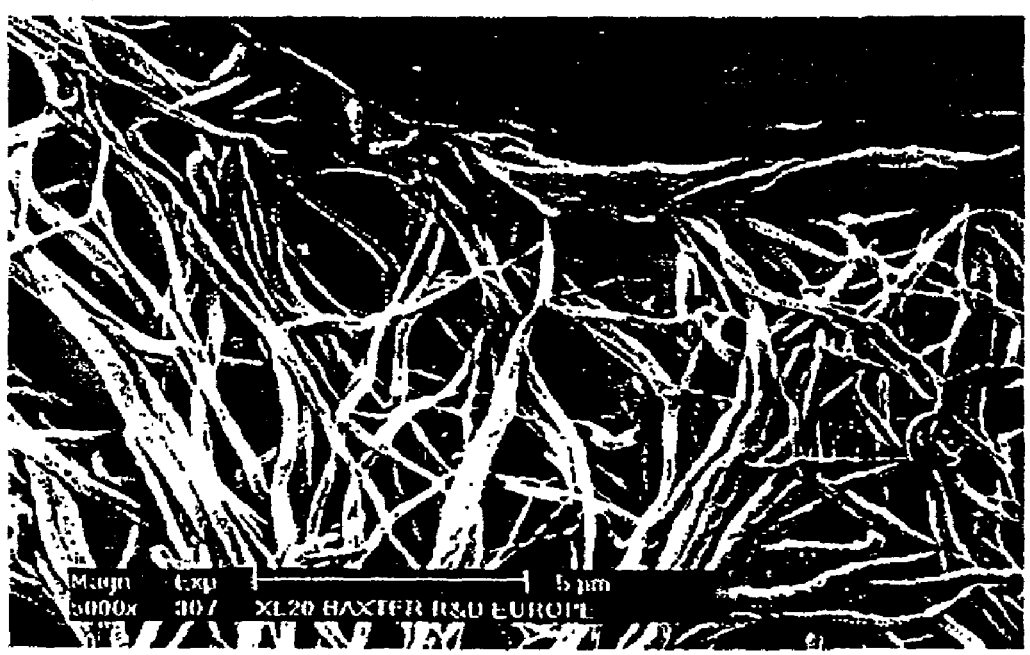
FIGS. 6, 7 and 8 are cross-sectional views of a slice of fibrin networks, as taken with an electron microscope, with a magnification of 5,000 times, after lyophilization.
Figure 7:
Figure 8:
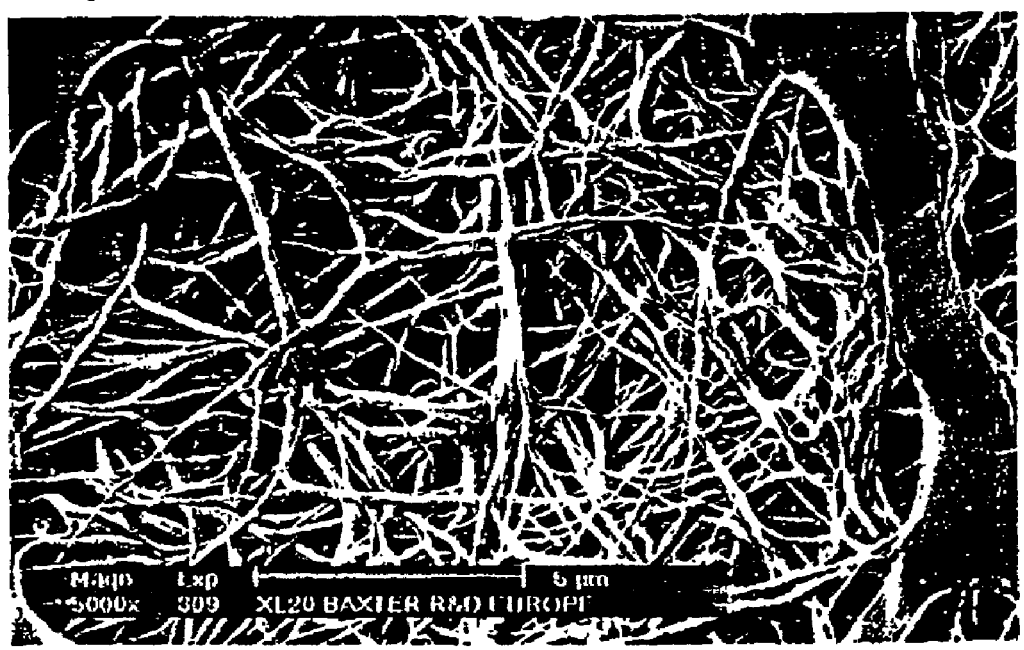

FIGS. 3, 4 and 5 are cross-sectional views of slices of fibrin networks from examples 2, 3 and 4 respectively, as taken with an electron microscope (Philips XL20 scanning Electron Microscope), with a magnification of 5,000 times, before lyophilization, whereas FIGS. 6, 7 and 8 are cross-sectional views of slices of fibrin networks from examples 2, 3 and 4 respectively, as taken with an electron microscope, with a magnification of 5,000 times, after lyophilization. By comparing these figures, the result is that the alveoli of the fibrin network from examples 2, 3 and 4 before lyophilization are similar, that the alveoli of the fibrin network from examples 2, 3 and 4 after lyophilization are similar, and that the use of glycerol allows the size of the network fibers to be reduced. Hence, glycerol, besides being useful to protect fibers during the lyophilization step, is an agent allowing control of the size or the diameter of the fibers of the fibrin network.

EXAMPLE 6

Example 4 was repeated, except that glycerol was replaced first by glucose and then by mannitol.

EXAMPLE 7

Example 1 was repeated, except for the use of a solution containing fibrinogen in the order of 10 mg/ml and thrombin in the order of 1 IU/ml, 10 IU/ml and 20 IU/ml respectively.

The networks obtained thereby were treated with a solution containing 2 to 2.5% of glutaraldehyde and with ethanol-containing solutions as described in example 4. Some slices of the networks so obtained were examined with an electron microscope (scanning electron microscope, Philips XL20). FIGS. 9, 10, and 11 are cross sectional views of the networks obtained with a solution containing 1 IU/ml, 10 IU/ml and 20 IU/ml of thrombin respectively, with a magnification of 3,500 times.

These FIGS. 9 to 11 show that a higher concentration of thrombin in the solution produces a greater number of fibers, but a smaller size thereof.

EXAMPLE 8

Example 1 was repeated, except that thrombin and fibrinogen solutions were prepared, which had a $CaCl_2$ concentration of 0 mM/ml, 2.7 mM/ml and 27 mM/ml. After treating and washing the networks as described in example 4, the cross section of the networks obtained with a solution containing 0 mM/ml (FIG. 12), 2.7 mM/ml (FIG. 13) and 27 mM/ml (FIG. 14) was examined with an electron microscope (Philips XL20), with a magnification of 5,000 times. These figures show that a higher calcium content corresponds to a greater number of fibers, a larger size thereof, and a smaller volume of the alveoli.

EXAMPLE 9

Example 4 was repeated, except for the use of a solution containing 5% of glycerol, 20 mg/ml of fibrinogen, 500 μg of fibronectin per ml, 10 IU/ml of factor XIII, 1 IU of thrombin per ml and 40 mM (millimoles) of calcium per ml.

EXAMPLE 10

Example 4 was repeated, except that the chamber vacuum was controlled to cause its intermittent variation from 600 mbar with respect to atmospheric pressure (a pressure of about $0.4\ 10^5$ Pa) to 630 mbar with respect to atmospheric pressure (a pressure of about $0.38\ 10^5$ Pa). This vacuum variation was found to be advantageous for fibrin and fibrinogen diffusion in the pores of the support. After washing with water, bringing the fibrin layer in contact with a water flow and creating a vacuum in the chamber varying from 600 mbar with respect to atmospheric pressure (a pressure of about $0.4\ 10^5$ Pa) to 630 mbar with respect to atmospheric pressure (a pressure of about $0.38\ 10^5$ Pa), the support and the fibrin layer contained no more free fibrinogen.

The tube may be easily sterilized, if needed, before or after lyophilization, at a temperature of 121° C. for 60 minutes, for example in an autoclave. Any other sterilization method may be used, provided that it does not destroy the alveoli structure of the cross-linked fibrin layer, nor the support structure.

EXAMPLE 11

Example 3 was repeated, except that the fibrinogen concentration was controlled in the tube, during the diffusion step, so as to ensure a substantially constant fibrinogen concentration in the tube. In order to do this, valve 23 was intermittently opened to evacuate a certain amount of solution out of the tube and a solution containing little or no fibrinogen was fed into the tube. This ensures that the fibrin layer is substantially regular and homogeneous in thickness.

EXAMPLE 12

Example 11 was repeated, except that the fibrinogen concentration was controlled substantially continuously, to decrease this concentration as fibrin is deposited on the inner wall of the tube.

EXAMPLE 13

Example 3 was repeated, except that, before treating the tubes with the fibrinogen solution, demineralized water, an aqueous solution containing 1 mg/ml of albumin, an aqueous solution containing 10 mg/ml of albumin, an aqueous solution containing 30 mg/ml of albumin, were respectively fed into the tubes, so as to fill or saturate the pores with said solution, before treating the tubes with the fibrinogen solution.

EXAMPLE 14

Example 3 was repeated, except that the proteins contained in the solution were 30 mg/ml of albumin and 10 mg/ml of fibronectin. Other proteins, such as vibronectin, etc. could be used, individually or in mixture, instead of albumin and/or fibronectin.

As set out in WO96/07444, the fibrin layer can be treated either to denature it or to provide it with particular properties.

The fibrin layer may be treated with water, with one or more salts (possibly in solution), with additives used to improve the biocompatibility of the support provided with the fibrin layer. The additives may be selected, for example, amongst proteins, anticoagulants, anti-inflammatory compounds, compounds reducing graft rejection, living cells, cell growth inhibitors, agents stimulating endothelial cells, antibiotics, antineoplastics, genetic materials, proteins promoting or stimulating the growth and/or attachment of endothelial cells on the cross-linked fibrin layer, growth factors, growth factors for heparin bond, substances against cholesterol (ZOCOR®), etc. Some particular examples of additives are given in U.S. Pat. No. 5,660,873, whose content is included in this application by way of reference.

The fibrin layer may be partially hydrolyzed, if needed, for example by means of a plasmin.

EXAMPLE 15

Example 1 was repeated, except that, during a first step, solution A was fed into the tube to obtain, by creating vacuum in the chamber, a non-cross-linked fibrin or fibrinogen layer, and that, during a second step, solution B (thrombin) was fed into the tube to form fibrin monomers and to obtain a cross-linked structure.

EXAMPLE 16

Example 4 was repeated, except that lyophilization was effected in several steps, i.e. by lowering temperature to −58° C., by maintaining this temperature of −58° C., by creating a vacuum (the lyophilization device had been adjusted with a pressure set-point of 7 Pa, so that the vacuum pump could operate continuously) for 1 to 5 hours, by raising temperature from −58° C. to −20° C. to −30° C., while maintaining the vacuum, by maintaining the temperature of −20° C. to −30° C., while maintaining the vacuum, for at least 10 hours (10 to 100 hours), by increasing the temperature to more than 20° C., while maintaining the vacuum.

EXAMPLE 17

Example 1 was repeated, except that the porous tube was successively treated with solution A and with solution B.
The treatment steps of this example are:
a) feeding solution A (fibrinogen) into the tube;
b) creating a vacuum in the space outside the tube to suck solution A through the walls of the tube;
c) removing solution A still present in the tube;
d) incubating the fibrinogen layer deposited for 15 minutes at ambient temperature (steps a), b), c) and d) may be repeated once or several times, for example twice or three times before step e));
e) feeding solution B (thrombin) into the tube;
f) creating a vacuum in the space outside the tube to suck solution B through the walls of the tube;
g) removing solution B still present in the tube;
h) incubating the layer at 37° C. for 30 minutes;
i) feeding solution A (fibrinogen) into the tube;
j) creating a vacuum in the space outside the tube to suck solution A through the walls of the tube;
k) removing solution A still present in the tube;
l) incubating the layer for 15 minutes at ambient temperature (steps i, j, k, and l may be repeated once or several times);
m) incubating the layer for 90 minutes at 37° C.

EXAMPLE 18

Example 16 was repeated, except that the intermediate incubation steps d, h and l were skipped.

EXAMPLE 19

Example 1 was repeated, except that the porous tube was successively treated with solution A and with solution B.
The treatment steps of this example are:
a) feeding solution A (fibrinogen) into the tube;
b) creating a vacuum in the space outside the tube to suck solution A through the walls of the tube;
c) removing solution A still present in the tube;
d) incubating the fibrinogen layer deposited for 15 minutes at ambient temperature;
e) feeding solution B (thrombin) into the tube;
f) creating a vacuum in the space outside the tube to suck solution B through the walls of the tube;
g) removing solution B still present in the tube;
h) incubating the layer at 37° C. for 30 minutes;
i) washing the tube with water (preferably in successive washing operations);
j) steps a to i are repeated once or several times;
k) incubating the layer for 90 minutes at 37° C.

EXAMPLE 20

Example 4 was repeated, except that the pH of the solution mixture was changed, upon its introduction, to 6, 6.5, 7, and 7.5 respectively, or except that the pH of the solution in the tube was controlled during the process to maintain it, for example, at 6.5 or 7 or 7.5.

EXAMPLE 21

Example 1 was repeated, except that, instead of placing the porous tube in a vacuum chamber, the tube was placed in a container with a concentrated aqueous solution of salt (NaCl) in order to create, by reverse osmosis, a water and fibrin-fibrinogen diffusion through the wall of the tube towards said concentrated solution.

EXAMPLE 22

The fibrinogen and thrombin compound of example 1 was injected by means of a syringe in a tube, to create a fibrin layer on the inner wall of the tube. This process causes fibrinogen to be present on the inner wall of the tube and in the fibrin layer in the proximity of said inner wall.

After removal of the fibrinogen solution and immersion of the tube in water (prewashing) the tube was placed in the vacuum chamber used in example 1. Then, demineralized water was fed into the tube, whereupon a vacuum was created in the chamber (pressure of $0.3\ 10^5$ Pa), so that water is sucked through the wall of the tube from the inner wall to the outer wall. This diffusion of water through the tube wall allows the unbound fibrinogen to be removed from the fibrin layer and outside the support, so that at least the part of the tube situated in the proximity of the inner wall of the tube is free of fibrinogen.

EXAMPLE 23

Example 22 was repeated, except that an aqueous solution containing 5% of glycerol was used for the washing operation by diffusion of water through the tube wall.

EXAMPLE 24

Example 22 was repeated, except that an aqueous solution containing 5% of glycerol and 1% of albumin was used for the washing operation by diffusion of water through the tube wall.

In the above examples, fibrin layers were prepared by using fibrinogen and thrombin from human blood. These could be replaced by products available on the market, such as biological glues by CRYOLIFE, e.g. the product FibRx, or by VITEX (the product VIGuard), or even recombinant fibrinogen.

The elements or membranes according to the invention, for example the membranes of examples 1 to 13 may be used in several applications, namely as membranes is for bioreactors, for example as described in the application EP 96910867, as membranes for filters, as implants such as artificial internal organs, as artificial veins, as artificial arteries, as antithrombotic materials, as cardiac valves, as artificial skins; the membrane may also be applied to the production of test kits or equipment, etc...

A number of tests was performed to determine the morphology of the cells attached to a lyophilized fibrin network prepared with no added glycerol (example 3), to a fibrin network prepared with a solution containing about 5% of glycerol (example 4) before and after lyophilization, and to a fibrin network prepared with a solution containing about 10% of glycerol (example 6) with lyophilization.

In these tests, a culture medium was prepared, from Dulbecco Modified Eagle Medium (DMEM). The following components, in the weight % as specified hereafter, were added to this DMEM medium:

20% of HAM'S F 12 (culture medium)
10% of FCS (Foetal Calf serum)
1% of non essential amino acids (i.e. L-alanine, L-asparagine, L-aspartic acid, L-glutamic acid, Glycine, L-proline, L-serine)
1% of sodium pyruvate
1% of Penicillium streptomycin, and
1% of L-glutamine.

This medium will be hereafter termed "prepared DMEM medium".

The cells used in these tests were isolated as follows:

just after the slaughter of cows, the bovine aorta was recovered. After separating the adipose tissues of the aortas, the collateral arteries were ligatured. The inner surface of the aortas was treated for 15 minutes at 37° C. with a solution containing 250 IU/ml of collagenase. The cells released in this treatment were recovered and placed in a DMEM culture medium containing valine D, 10% of FCS, 100 IU/ml of penicillin, 100 µg/ml of streptomycin and 2.5 µg/ml of amphotericin B. The culture medium was renewed after 24 hours.

After two days, the culture medium was placed in a 70% DMEM culture medium, containing 20% of Ham's F 12, 10% of FCS. 100 IU/ml of penicillin, 100 µg/ml of streptomycin and 2.5 µm/ml of amphotericin B.

Once the cells reach confluence, they are recovered with the help of trypsin (1 mg/ml) in the presence of EDTA (ethylenediaminetetraacetic acid).

Then, they are grown in the "prepared DMEM medium".

Before adding the cells in Petri dishes containing a support with a fibrin network, the cells were recovered from the DMEM medium prepared by incubation in a trypsin-EDTA medium (5 times as concentrated) for 5 minutes at 37° C., then 10 ml of a culture medium containing 10% of FCS were added to stop the action of the enzyme. The number of cells in the medium was determined with the help of a microscope by counting the cells in a Bürker chamber after trypan blue marking. This method will be hereafter named microscope counting method. The resulting number of cells was 25,000 cells/ml for a first solution and 125,000 cells/ml for a second solution.

2 ml of the culture medium, containing 50,000 cells and 250,000 cells respectively were added separately in the different Petri dishes respectively containing a lyophilized fibrin network prepared with no added glycerol (Dish 1), a fibrin network prepared with a solution containing about 5% of glycerol (example 4) before lyophilization (Dish 2) and after lyophilization (Dish 3), and a fibrin network prepared with a solution containing about 10% of glycerol (example 5) with lyophilization (Dish 4).

The culture of cells in Petri dishes occurred at 37° C. for 2 hours for a first batch of dishes (dishes containing 50,000 cells) and for 11 days for a second batch of dishes (dishes containing 250,000 cells). When the culture time—either 2 hours, or 11 days—expired, the fibrin networks in Petri dishes were fixed by means of a 2.5% glutaraldehyde solution. FIGS. 15, 16, 17 and 18 are top views of the fibrin layer of the dishes 1, 2, 3, and 4 after 2 hours culture, as taken with an electron microscope (Philips XL20 scanning Electron Microscope). These figures show good cell attachment on fibrin networks in the different dishes, after two hours of culture. The cells are distributed on the upper surface with a regular and flat arrangement.

For the dishes in culture for 11 days at 37° C., a visual examination of dishes was performed during the culture time. This examination showed that, after 8 days of culture, fibrinolysis of the network of dish 1 (fibrin network without glycerol) was visible, whereas no fibrinolysis was perceptible for the networks of dishes 2, 3 and 4 after 8 days of culture.

After 11 days of culture, the number of viable cells was counted for dish 1 and for dishes 2 and 3. The number of viable cells was determined by means of an enzymatic kit, Boehringer Mannheim WST-1 (Catalogue no. 1644807-batch no. 14890800). The principle of this method is based on the cleavage of a tetrazolium salt, added to the medium, into formazan, by a mitochondrial enzyme (succinate-tetrazolium reductase). This reduction only takes place in viable cells. The formazan color to produced by metabolically active cells is quantified by a scanning spectrophotometer (ELISA reader). This determination was made by replacing the culture medium of Petri dishes 1, 2 and 3 by 1 ml of a fresh medium containing 100 µl of the solution of the WST-1 enzymatic kit. After four hours of incubation at 37° C. under an atmosphere containing 7% of $CO_2$, 100 µl of the colored solution of each dish were collected for a spectrometer analysis. The difference between the absorbance peak at 450 nm and the absorbance at 655 nm was determined for each solution. The absorbance difference for dishes 2 and 3 was found to be much more important (40 to 50% higher) than for dish 1. The absorbance difference for dishes 1, 2 and 3 was at least four times higher than that of a sample with no cells therein. This analysis proves that the cells in dishes 1, 2 and 3 are viable, and further that the presence of glycerol ensures better cellular viability.

The invention claimed is:

1. An element comprising:
 a support having a thickness and a face;
 the face having at least two pores extending through the entire support thickness and spaced from one another to define a node spacing, one of the at least two pores having a diameter from about 10 μm to about 20 μm, the other pore having a diameter greater than about 20 μm; and
 a substantially fibrinogen-free non-hydrolyzed fibrin network in direct contact with the face and extending into each pore a distance from about 2 μm to about 20 μm.

2. The element according to claim 1 wherein the support is substantially hydrophobic.

3. The element according to claim 1 wherein the support has a thickness from about 0.1 mm to about 5 mm.

4. The element according to claim 1 wherein the fibrin network extends over the pores.

5. The element according to claim 1 wherein the node spacing is from about 5 μm to about 100 μm.

6. The element of claim 1 wherein the fibrin network has a substantially uniform thickness across the entire face.

7. The element according to claim 1 wherein the fibrin network contains less than 1% by weight of unreacted fibrinogen.

8. The element according to claim 1 wherein the fibrin network contains from less than about 0.5% to less than about 0.1% by weight of unreacted fibrinogen.

9. The element according to claim 1 wherein the fibrin network contains no unreacted fibrinogen.

10. The element according to claim 1 wherein the node spacing is substantially homogeneous and uniform.

11. The element according to claim 1 wherein the fibrin network extends from about 10 μm to about 20 μm into the at least one pore.

12. The element according to claim 1 wherein the pores are free of fibrinogen.

13. The element according to claim 1 wherein the fibrin network further includes a first surface and a second surface.

14. The element according to claim 13 wherein first surface is in contact with the support.

15. The element according to claim 14 wherein second surface is stabilized by at least partial cross-linking to form a network of adjacent alveoli.

16. The element according to claim 15 wherein the at least partially cross-linked fibrin network is 0.5 to 100 μm thick when measured in the dry state.

17. The element according to claim 16 wherein the at least partially cross-linked fibrin network is 2.5 to 50 μm thick when measured in the dry state.

18. The element according to claim 15 wherein the alveoli are formed between the cross-linked fibrin.

19. The element according to claim 18 wherein the alveoli have a volume from about 5 μm³ to about 25 μm³.

20. The element according to claim 19 wherein the alveoli have an average thickness from about 1 μm to about 5 μm when measured in the dry state.

21. The element according to claim 13 wherein the fibrin network is provided with cells.

22. The element according to claim 21 wherein the cells mediate cell-fibrin bonds.

23. The element according to claim 13 wherein the fibrin network is provided with proteins.

24. The element according to claim 23 wherein the proteins mediate cell-fibrin bonds.

25. The element according to claim 1 wherein the pores further comprise inner pore faces, the inner pore faces at least partially covered by a component selected from the group consisting of water-soluble or substantially water-soluble protein, and an organic additive.

26. The element according to claim 1 wherein the fibrin network is at least partially covered by a water-soluble or substantially water-soluble protein.

27. The element according to claim 1 wherein the fibrin network further comprises a polar additive.

28. The element according to claim 1 wherein the polar additive is selected from the group consisting of glycerol, sugars, sucrose, glucose, mannitol and mixtures thereof.

29. The element according to claim 1 wherein the fibrin network has a moisture content of less than 0.5%.

30. The element according to claim 1 wherein the fibrin network contains fibronectin.

31. The element according to claim 30 wherein the fibronectin content is from about 0.5% to about 15%.

32. The element according to claim 1 wherein the fibrin network contains calcium.

33. The element according to claim 32 herein the calcium content is from about 1 μg to about 100 μg per cm³ of the fibrin network volume.

34. The element according to claim 32 wherein the calcium is calcium chloride.

35. The element according to claim 1 wherein the support further includes a second fibrin network superimposed on the fibrin network.

36. The element according to claim 35 wherein the fibrin network is in contact with the support.

37. The element according to claim 36 wherein the fibrin network contains alveoli.

38. The element according to claim 35 wherein the second fibrin network contains alveoli.

39. The element according to claim 35 wherein the alveoli of the fibrin network have larger volumes than the alveoli of the second fibrin network.

40. The element according to claim 1 wherein the support is biocompatible and/or biodegradable.

41. The element of claim 1 wherein the element is a membrane for a device selected from the group consisting of a bioreactor and a filter.

42. The element of claim 1 wherein the element is an implant for a component selected from the group consisting of an artificial internal organ, an artificial vein, an artificial artery, an antithrombotic material, and a cardiac valve.

43. The element of claim 1 wherein the element is an artificial skin.

44. A filter including a membrane element comprising:
 a support having a thickness and a face;
 the face having at least two pores extending through the entire support thickness and spaced from one another to define a node spacing, one of the at least two pores having a diameter from about 10 μm to about 20 μm, the other pore having a diameter greater than about 20 μm; and
 a substantially fibrinogen-free non-hydrolyzed fibrin network in direct contact with the face and extending into each pore a distance from about 2 μm to about 20 μm.

* * * * *